Figure 1A:
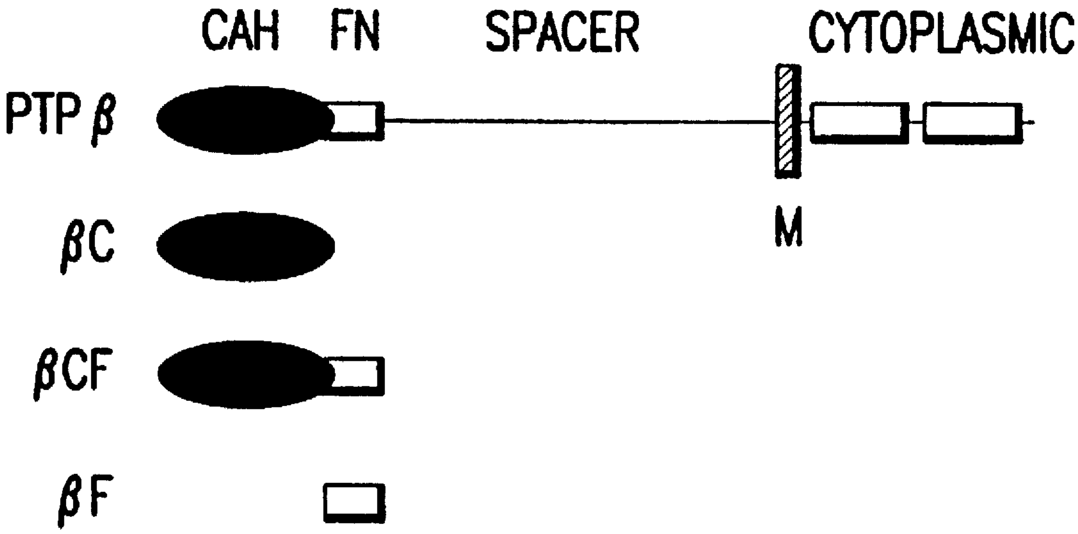

US005766922A

United States Patent [19]

Peles

[11] Patent Number: 5,766,922

[45] Date of Patent: Jun. 16, 1998

[54] FUNCTIONAL LIGANDS FOR THE AXONAL CELL RCOGNITION MOLECULE CONTACTIN

[75] Inventor: Elior Peles, Foster City, Calif.

[73] Assignee: Sugen, Inc., Redwood City, Calif.

[21] Appl. No.: 452,052

[22] Filed: May 26, 1995

[51] Int. Cl.$^6$ .......................... C12N 1/38; G01N 33/566; G01N 33/567

[52] U.S. Cl. ............................ 435/244; 435/7.1; 435/7.2; 435/7.21; 435/7.92; 436/63; 436/503

[58] Field of Search .................................... 435/7.1, 7.21, 435/244, 7.92; 436/63; 530/324, 350, 387.1, 391.1, 402, 839

[56] References Cited

FOREIGN PATENT DOCUMENTS

WO 95/35373 12/1995 WIPO ............................ C12N 15/12

OTHER PUBLICATIONS

Peles et al (1995, Jul. 28) Cell 82: 251–260.

Stryer (1988) Biochemistry, W.H. Freeman and Co., New York, pp. 50–55.

Pierce Immunotechnology Catalog (1992–1993) p. E–26.

Barnea, G., M. Grumet, J. Sap, R. U. Margolis, and J. Schlessinger. 1993. Close similarity between receptor–linked tyrosine phosphatase and rat brain proteoglycan. Cell 76:205.

Barnea, G., et al. 1994. Receptor tyrosine phosphatase b is expressed in the form of proteoglycan and binds to the extracellular matrix protein tenascin. The Journal of Biological Chemistry 269:14349–14352.

Barnea, G. et al.. 1993. Identification of a Carbonic Anhydrase–Like Domain in the Extracellular Region of RPTPg Defines a New Subfamily of Receptor Tyrosine Phosphatases. Molecular and Cellular Biology 13:1497–1506.

Berglund, E. O., and B. Ranscht. 1994. Molecular cloning and in situ localization of the human contactin gene (CNTN1) on chromosome 12q11–q12. Genomics 21:571–582.

Brady–Kalnay, S. M., A. J. Flint, and N. K. Tonks. 1993. Homophilic binding of PTPm, a receptor–type protein tyrosine phosphatase, can mediate cell–cell aggregation. The Journal of Cell Biology 122:961–972.

Brümmendorf, T., M. J. Wolff, R. Frank, and F. G. Rathjen. 1989. Neural cell recognition molecule F11: homology with fibronectin type III and immunoglobulin type C domains. Neuron 2:1351–1361.

Brümmendorf, T., M. Hubert, U. Treubert, R. Leuschner, A. Tarnok, and F. G. Rathjen. 1993. The axonal recognition molecule F11 is a multifunctional protein: specific domains mediate interactions with Ng–CAM and restrictin. Neuron 10:711–727.

Brümmendorf, T., and F. G. Rathjen. 1993. Axonal glycoproteins with immunoglobulin– and fibronectin type III–related domains in vertebrates: structural features, binding activities and signal transduction. Journal of Neurochemistry 61:1207–1219.

Canoll, P. D. et al. 1993. The expression of a novel receptor–type tyrosine phosphatase suggests a role in morphogenesis and plasticity of the nervous system. Developmental Brain Research 75:293–298.

Carbonneau, H., and N. K. Tonks. 1992. 1002 protein phosphatases? Annu. Rev. Cell Biol. 8:463–93.

Chao, M. V. 1992. Neurotrophin receptors: a window into neuronal differentiation. Neuron 9:583–593.

Chomczynski, P., and N. Sacchi. 1987. Single–step method of RNA isolation by acid guanidinium thiocyanate–phenol–cholorform extraction. Analytical Biochemistry 162:156–159.

Clarke, G. A., C. A. White, and D. J. Moss. 1993. Substrate–bound GP130/F11 will promote neurite outgrowth: evidence for a cell surface receptor. European Journal of Cell Biology 61:108–115.

D'Allesandri, L., B. Ranscht, K. H. Winterhalter, and L. Vaughan. 1995. Contactin/F11 and tenascin–C co–expression in the chick retina correlates with formation of the synaptic plexiform layers. Current Eye Research 14:911–926.

den Hertog, J., C. E.G.M.Pals, M. P. Peppelenbosch, G. J. Tertoolen, Leon, S. W. de Laat, and W. Kruijer. 1993. Receptor protein tyrosine phosphatase a activates pp60c–src and is involved in neuronal differentiation. EMBO 12:3789–3798.

Dodd, J., S. B. Morton, D. Karagogeos, M. Yamamoto, and T. M. Jessell. 1988. Spatial regulation of axonal glycoprotein expression on subsets of embryonic spinal neurons. Neuron 1:105–116.

Doherty, P., and F. S. Walsh. 1994. Signal transduction events underlying neurite outgrowth stimulated by cell adhesion molecules. Current Opinion in Neurobiology 4:49–55.

Durbec, P., G. Gennarini, C. Goridis, and G. Rougon. 1992. A soluble form of the F3 neuronal cell adhesion molecule promotes neurite outgrowth. The Journal of Cell Biology 117:877–887.

Durbec, P., G. Gennarini, M. Buttiglione, S. Gomez, and G. Rougon. 1993. Different domains of the F3 neuronal adhesion molecule are involved in adhesion and neurite outgrowth promotion. European Journal of Neuroscience 6:461–472.

(List continued on next page.)

*Primary Examiner*—Paula K. Hutzell
*Assistant Examiner*—Jacqueline G. Krikorian

[57] ABSTRACT

The extracellular domain of RPTPβ is the ligand for contactin and its binding results in neurite growth and differentiation. The invention encompasses compounds that mimic, enhance, or suppress the effects of the ligand for contactin, assays for the identification of such compounds, and the use of such compounds to treat neurologic diseases including those characterized by insufficient, aberrant, or excessive neurite growth, differentiation or survival.

5 Claims, 15 Drawing Sheets

OTHER PUBLICATIONS

Friedlander, D. R., et al. 1994. The neuronal chondroitin sulfate proteoglycan neurocan binds to the neural cell adhesion molecules Ng-CAM/L1/NILE and N-CAM, and inhibits neuronal adhesion and neurite outgrowth. The Journal of Cell Biology 125:669-680.

Furley, A. J., S. B. Morton, D. Manalo, D. Karagogeos, J. Dodd, and T. M. Jessell. 1990. The axonal glycoprotein TAG-1 is an immunoglobulin superfamily member with neurite outgrowth-promoting activity. Cell 61:157-170.

Gebbink, M., F.B.G., G. Zondag, C.M., R. W. Wubbolts, R. L. Beijersbergen, I. van Etten, and W. H. Molenaar. 1993. Cell–cell adhesion mediated by a receptor–like protein tyrosine phosphatase. The Journal of Biological Chemistry 268:16101-16104.

Gennarini, G., G. Rougon, F. Vitiello, C. Di Benedetta, and C. Goridis. 1989. Identification and cDNA cloning of a new member of the L2/HNK-1 family of neural sufrace glycoproteins. Journal of Neuroscience Research 22:1-12.

Gennarini, G., G. Cibelli, G. Rougon, and M.-G. Mattei. 1989. The mouse neuronal cell surface protein F3: A phosphatidylinositol-anchored member of the immunoglobulin superfamily related to chicken contactin. The Journal of Cell Biology 109:775-788.

Gennarini, G., P. Durbec, and C. Goridis. 1991. Transfected F3/F11 neuronal cell surface protein mediates intercellular adhesion and promotes neurite outgrowth. Neuron 6:595-606.

Gloor, S., H. Antonicek, K. J. Sweadner, S. Pagliusi, R. Frank, and M. Moos. 1990. The adhesion molecule on glia (AMOG) is a homologue of the b subunit of the Na, K-ATPase. The Journal of Cell Biology 110:165-174.

Goodman, C. S., and C. J. Shatz. 1993. Developmental mechanisms that generate precise patterns of neuronal connectivity. Cell 72:77-98.

Grumet, M., S. Hoffman, and G. M. Edelman. 1984. Two antigenically related neuronal cell adhesion molecules of different specificities mediate neuron–neuron and neuron–glia adhesion. Proc. Nat. Acad. Sci. USA 81:267-271.

Grumet, M., A. Flaccus, and R. U. Margolis. 1993. Functional characterization of chondroitin sulfate proteoglycans of brain: interactions with neurons and neural cell adhesion molecules. The Journal of Cell Biology 120:815-824.

Grumet, M., et al. 1994. Interactions with tenascin and differential effects on cell adhesion of neurocan and phosphacan, two major chondroitin sulfate proteoglycans of nervous tissue. The Journal of Biological Chemistry 269:12142-12146.

Hawrot, E., and P. H. Patterson. 1979. Long–term culture of disassociated sympathetic neurons. Methods in Enzymology 53:574-585.

Hosoya, H., K. Shimazaki, S. Kobayashi, H. Takahashi, T. Shirasawa, T. Takenawa, and K. Watanabe. 1995. Developmental expression of the neural adhesion molecule F3 in the rat brain. Neuroscience Letters 186:83-86.

Hunter, T. 1995. Protein kinases and phosphatases: the yin and yang of protein phosphorylation and signaling. Cell 80:225-236.

Huse, W. D., L. Sastry, S. A. Iverson, A. S. Kang, M. Alting-Mees, D. R. Burton, S. J. Benkovic, and R. A. Lerner. 1989. Generation of a large combinatorial library of the immunoglobulin repertoire in phage lambda. Science 246:1275-1281.

Hynes, R. O., and A. D. Lander. 1992. Contact and adhesive specificities in the associations, migrations, and targeting of cells and axons. Cell 68:303-322.

Ignelzi, M. A., D. R. Miller, P. Soriano, and P. F. Maness. 1994. Impaired neurite outgrowth of src–minus cerebellar neurons on the cell adhesion molecule L1. Neuron 12:873-884.

Keynes, R. J., and G. M. W. Cook. 1992. Repellant cues in axon guidance. Current Opinion in Neurobiology 2:55-59.

Kris, R. M., I. Lax, W. Gullick, M. D. Waterfield, A. Ullrich, M. Fridkin, and J. Schlessinger. 1985. Antibodies against a synthetic peptide as a probe for the kinase activity of the avian EGF receptor and v–erbB protein. Cell 40:619-625.

Krishna Rao, A. S. M., and R. E. Hausman. 1993. cDNA for R–cognin: homology with a multifunctional protein. Proc. Natl. Acad. Sci. USA 90:2950-2954.

Krueger, N. X. 1992. A human transmembrane protein–tyrosine–phosphatase, PTPz, is expressed in brain and has an N–terminal receptor domain homologous to carbonic anhydases. Proc. Natl. Acad. Sci. USA 89:7417-7421.

Lammers, R., B. Bossenmaier, D. E. Cool, N. K. Tonks, J. Schlessinger, E. H. Fischer, and A. Ullrich. 1993. Differential activities of protein tyrosine phosphatases in intact cells. The Journal of Biological Chemistry 268:22456-22462.

Levy, J. B. et al. 1993. The Cloning of a Receptor–type Protein Tyrosine Phosphatase Expressed in the Central Nervous System. The Journal of Biological Chemistry 268:10573-10581.

Lüdecke, G., and K. Unsicker. 1990. Mitogenic effect of neurotrophic factors on human IMR 32 neuroblastoma cells. Cancer 65:2270-2278.

Maa, J.-S., J. F. Rodriguez, and M. Esteban. 1990. Structural and functional characterization of a cell surface binding protein of vaccinia virus. The Journal of Biological Chemistry 265:1569-1577.

Maurel, P. et al. 1994. Phosphacan, a chondroitin sulfate proteoglycan of brain that interacts with neurons and neural cell–adhesion molecules, is an extracellular variant of a receptor–type protein tyrosine phosphatase. PNAS 91:2512-2516.

Milev, P. et al. 1994. Interactions of the chondroitin sulfate proteoglycan phosphacan, the extracellular domain of a receptor–type protein tyrosine phosphatase, with neurons, glia, and neural cell adhesion molecules. J. Cell Biol. 127:1703-1715.

Morales, G. et al. 1993. Induction of axonal growth by heterophilic interactions between the cell surface recognition proteins F11 and Nr–CAM/Bravo. Neuron 11:1113-1122.

Muller, A. J. et al. 1991. BCR first exon sequences specifically activate the BCR/ABL tyrosine kinase oncogene of Philadelphia chromosome–positive human leukemias. Molecular and Cellular Biology 11:1785-1792.

Nörenberg, U., H. Willie, J. M. Wolff, R. Frank, and F. G. Rathjen. 1992. The chicken neural extracellular matrix molecule restrictrin: similarity with EGF–, fibronectin type III–, and fibrinogen–like motifs. Neuron 8:849-863.

Olive, S. et al. 1995. Expression of a glycosyl phosphatidylinositol–anchored adhesion molecule, the glycoprotein F3, in the adult rat hypothalamo–neurohypophysial system. Brain Research 689:271-280.

Peles, E., R. Ben Levy, E. Or, A. Ullrich, and Y. Yarden. 1991. Oncogenic forms of the neu/HER2 tyrosine kinase are permanently coupled to phospholipase Cg. The EMBO Journal 10:2077-2086.

Peles, E., S. S. Bacus, R. A. Koski, H. S. Lu, D. Wen, S. G. Ogden, R. Ben Levy, and Y. Yarden. 1992. Isolation of the Neu/HER2 stimulatory ligand: a 44 kd glycoprotein that induces differentiation of mammary tumor cells. Cell 69:205–216.

Pesheva, P., G. Gennarini, C. Goridis, and M. Schachner. 1993. The F3/11 cell adhesion molecule mediates the repulsion of neurons by the extracellular matrix glycoprotein J1-160/180. Neuron 10:69–82.

Plowman, G. D. et al. 1992. The epithelin precursor encodes two proteins with opposing activities on epithelial cell growth. The Journal of Biological Chemistry 267:13073–13078.

Pulido, D., S. Campuzano, T. Koda, J. Modelell, and M. Barbacid. 1992. Dtrk, a Drosophila gene related to the trk family of neurotrophin receptors, encodes a novel class of neural cell adhesion molecule. The EMBO Journal 11:391–404.

Ranscht, B. et al. 1988. Sequence of contactin, a 130–kD glycoprotein concentrated in areas of interneuronal contact, defines a new member of the immunoglobulin supergene family in the nervous system. J. Cell Bio. 107:1561–1573.

Rathjen, F. G., J. M. Wolff, R. Frank, F. Bonhoeffer, U. Rutishauser, and A. Schoeffski. 1987. Membrane glycoproteins involved in neurite fasciculation. The Journal of Cell Biology 104:343–353.

Rathjen, F. G., J. M. Wolff, and R. Chiquet–Ehrismann. 1991. Restrictin: a chick neural extracellular matrix protein involved in cell attachment co–purifies with the cell recognition molecule F11. Development 113:151–164.

Reid, R. A., D. D. Bronson, K. M. Young, and J. J. Hemperly. 1994. Identification and characterization of the human cell adhesion molecule contactin. Molecule Brain Research 21:1–8.

Rougon, G., S. Olive, P. Durbec, C. Faivre–Sarrailh, and G. Gennarini. 1994. Functional studies and cellular distribution of the F3 FPI–anchored adhesion molecule. Brazilian J. Med. Biol. Res. 27:409–414.

Sahin, M., J. J. Dowling, and S. Hockfield. 1995. Seven protein tyrosine phosphatases are differentially expressed in the developing rat brain. The Journal of Comparative Neurology 351:617–631.

Sarrailh, C. F. 1992. F3/F11 cell surface molecule expression in the development mouse cerebellum is polaized at synaptic sites and within granule cells. The Journal of Neuroscience 12:257–267.

Sarrailh, C. F., and G. Rougon. 1993. Are the glypiated adhesion molecules preferentially targeted to the axonal compartment? Molecular Neurobiology 7:49–60.

Schachner, M., J. Taylor, U. Bartsch, and P. Pesheva. 1994. The perplexing multifunctionality of Janusin, a tenascin–related molecule. Perspectives on Development Neurobiology 2:33–41.

Schlessinger, J., and A. Ullrich. 1992. Growth factor signaling by receptor tyrosine kinases. Neuron 9:383–391.

Sharma, E., and P. J. Lombroso. 1995. A neuronal protein tyrosine phosphatase induced by nerve growth factor. The Journal of Biological Chemistry 270:49–53.

Shitara, K., H. Yamada, K. Watanabe, M. Shimonaka, and Y. Yamaguchi. 1994. Brain–specific receptor–type protein–tyrosine phosphatase RPTPb is a chondroitin sulfate proteoglycan in vivo. J. Biol. Chem. 269:20189–20193.

Shock, L. P., D. J. Bare, S. G. Klinz, and P. F. Maness. 1995. Protein tyrosine phosphatases expressed in developing brain and retinal Müller glia. Molecular Brain Research 28:110–116.

Simmons, D. L. 1993. Cloning cell surface molecules by transient expression in mammalian cells. Cellular Interactions in Development, A Practical Approach, 93–127.

Theodosis, D. T., L. Bonfanti, S. Olive, G. Rougon, and D. A. Poulain. 1994. Adhesion molecules and structural plasticity of the adult hypothalamo–neurohypophysial system. Psychoneuroendocrinology 19:455–462.

Theveniau, M. et al. 1992. Expression and release of phosphatidylinositol anchored cell surface molecules by a cell line derived from sensory neurons. Journal of Cellular Biochemistry 48:61–72.

Umemori, H., S. Sato, T. Yagi, S. Aizawa, and T. Yamamoto. 1994. Initial events of myelination involve Fyn tyrosine kinase signalling. Nature 367:572–576.

Vaughan, L., P. Weber, L. D'Alessandri, A. H. Zisch, and K. H. Winterhalter. 1994. Tenascin–contactin/F11 interactions: a clue for the development role? Perspectives on Developmental Neurobiology 2:43–52.

Walsh, F. S., and P. Doherty. 1991. Glycosylphosphatidylinositol anchored recognition molecules that function in axonal fasciculation, growth and guidance in the nervous system. Cell Biology International Reports 15:1151–1166.

Walton, K. M., K. J. Martell, S. Kwak, P., J. E. Dixon, and B. L. Largent. 1993. A novel receptor–type protein tyrosine phosphatase is expressed during neurogenesis in the olfactory neuroepithelium. Neuron 11:387–400.

Wolff, J. M., F. G. Rathjen, and S. Roth. 1987. Biochemical characterization of polypeptide components involved in neurite fasciculation and elongation. Eur. J. Biochem. 168:551–561.

Zhang, J. S. et al. 1995. LAR tyrosine phosphatase receptor: alternative splicing is preferential to the nervous system, coordinated with cell growth and generates novel isoforms containing extensive CAG repeats. J. Cell Biol. 128:415–431.

Zipursky, S. L., and G. M. Rubin. 1994. Determination of neuronal cell fate: lessons from the R7 neuronal drosophila. Annu. Rev. Neurosci. 17:373–397.

Zisch, A. H. et al. 1992. Neuronal cell adhesion molecule contactin/F11 binds to tenascin via its immunoglobulin–like domains. The Journal of Cell Biology 119:203–213.

1 MKTPLLVSHL LLISLTSCLG EFTWHRRYGH GVSEEDKGFG PIFEEQPINT IYPEESLEGK
W VI I T A Y
61 VSLNCRARAS PFPVYKWRMN NGDVDLTNDR YSMVGGNLVI NNPDKQKDAG IYYCLASNNY
S
121 GMVRSTEATL SFGYLDPFPP EDRPEVKVKE GKGMVLLCDP PYHFPDDLSY RWLLNEFPVF
E R
181 ITMDKRRFVS QTNGNLYIAN VESSDRGNYS CFVSSPSITK SVFSKFIPLI PIPERTTKPY
A K
241 PADIVVQFKD IYTMMGQNVT LECFALGNPV PDIRWRKVLE PMPTTAEIST SGAVLKIFNI
V AL S
301 QLEDEGLYEC EAENIRGKDK HQARIYVQAF PEWVEHINDT EVDIGSDLYW PCVATGKPIP
I
361 TIRWLKNGYA YHKGELRLYD VTFENAGMYQ CIAENAYGTI YANAELKILA LAPTFEMNPM
T A
421 KKKILAAKGG RVIIECKPKA APKPKFSWEK GTEWLVNSSR ILIWEDGSLE INNITRNDGG

481 IYTCFAENNR GKANSTGTLV ITNPTRILLA PINADITVGE NATMQCAASF DPSLDLTFVW
D A
541 SFNGYVIDFN KEITHIHYQR NFMLDANGEL LIRNAQLKHA GRYTCIAQTI VDNSSASADL
--N S
601 VVRGPPGPPG GLRIEDIRAT SVALTWSRGS DNHSPISKYT IQTKTILSDD WKDAKTDPPI

661 IEGNMESAKA VDLIPWMEYE FRVVATNTLG TGEPSIPSNR IKTDGAAPNV APSDVGGGGG
A R R
721 TNRELTITWA PLSREYHYGN NFGYIVAFKP FDGEEWKKVT VTNPDTGRYV HKDETMTPST
R S
781 AFQVKVKAFN NKGDGPYSLI AVINSAQDAP SEAPTEVGVK VLSSSEISVH WKHVLEKIVE
V E
841 SYQIRYWAGH DKEAAAHRVQ VTSQEYSARL ENLLPDTQYF IEVGACNSAG CGPSSDVIET
A E N P M A
901 FTRKAPPSQP PRIISSVRSG SRYIITWDHV VALSNESTVT GYKILYRPDG QHDGKLFSTH
K V Y
961 KHSIEVPIPR DGEYVVEVRA HSDGGDGVVS QVKISGVSTL SSGLLSLLLP SLGFLVFYSE
AP PS G AP I - L
1021 F

FIG.4B

FUNCTIONAL LIGANDS FOR THE AXONAL CELL RCOGNITION MOLECULE CONTACTIN

1. INTRODUCTION

The present invention relates to the identification and use of compounds that bind to contactin, a surface molecule of neural cells, and stimulate the growth, differentiation or survival of targeted neural cells. The carbonic anhydrase (CAH) domain of the receptor-type tyrosine phosphatase RPTPβ is identified as the ligand for contactin. The binding of the CAH domain of RPTPβ to the contactin on neural cells results in neurite growth, differentiation and survival. The invention relates to compounds that mimic, enhance, or suppress the effects of the RPTBβ ligand for contactin, including those molecules which act downstream in the signal transduction pathway that results from the binding of the ligand to contactin. The invention further relates to assays and methods for the identification of such compounds. In addition, the invention also relates to the use of such compounds to treat neurologic diseases including those characterized by insufficient, aberrant, or excessive neurite growth, differentiation or survival.

2. BACKGROUND OF THE INVENTION

The ability of cells to respond to signals from their microenvironment is a fundamental feature of development. In the developing nervous system, neurons migrate and extend axons to establish their intricate network of synaptic connections (Goodman and Shatz, 1993, Cell/Neuron (Suppl.), 72/10:77–98). During migration and axonal pathfinding, cells are guided by both attractive and repulsive signals (Hynes and Lander, 1992, Cell, 68:303–322; Keynes and Cook, 1992, Lurr. Opin. Neurobiol., 2:55–59). The ability of the neuron to respond to these signals requires cell surface molecules that are able to receive the signal and to transmit it to the cell interior resulting in specific biological responses.

It is well established that protein tyrosine phosphorylation is responsible for the regulation of many cellular responses to external stimuli crucial for cell growth, proliferation and differentiation (Schlessinger and Ullrich, 1992, Neuron, 9:383–391). Tyrosine phosphorylation has been implicated in several developmental processes in the nervous system. For example, receptor tyrosine kinases were shown to effect neuronal survival (Chao, 1992, Neuron, 9:583–593), and cell fate determination (Zipursky and Rubin, 1994, Annu. Rev. Neurosci., 17:373–397). Non-receptor tyrosine kinases have been shown to be downstream elements in signaling via cell recognition molecules that play a role in cell guidance and migration (Ignelzi et al., 1994, Neuron, 12:873–884; Umemori et al., 1994, Nature, 367–572–586).

The transient nature of signaling by phosphorylation requires specific phosphatases for control and regulation (Hunter, 1995, Cell, 80:225–236). Indeed, many protein tyrosine phosphatases have been shown to be expressed in specific regions of the developing brain, including the olfactory neuroepithelium (Walton et al., 1993, Neuron, 11:387–400), the cortex (Sahin et al., 1995, J. Comp. Neurol., 351:617–631), and in retinal Müller glia (Shock et al., 1995, Mol. Brain Res., 28:110–116). Furthermore, expression of several tyrosine phosphatases, such as PTPα (den Hertog et al., 1993, EMBO J., 12:3789–3798), PC12-PTP1 (Sharama and Lombroso, 1995, J. Biol. Chem., 270:49–53) and several forms of LAR (Zhang and Longo, 1995, J. Cell. Biol., 128:415–431) have been found to be regulated during neural differentiation of P19 or PC12 cells.

Receptor-type tyrosine phosphatases (RPTPs) have been subdivided into several groups based on structural characteristics of their extracellular domains (Charbonneau and Tonks, 1992, Annu. Rev. Cell Biol., 8:463–493; Barnea et al., 1993, Mol. Cell. Biol., 13:1497–1506). RPTPβ/ζ and RPTPγ are members of a distinct group of phosphatases, characterized by the presence of a carbonic anhydrase-like domains (CAH), fibronectin type III repeats (FNIII), and a long cysteine free region (spacer domain) in their extracellular domain (Barnea et al., 1993, Mol. Cell. Biol., 13:1497–1506; Krueger et al., 1992, Proc. Natl. Acad. Sci. USA, 89:7417–7421; Levy et al., 1993, J. Biol. Chem., 268:10573–10581). The expression of RPTPβ is restricted to the central and peripheral nervous system, while RPTPγ is expressed both in the developing nervous system, as well as, in a variety of other tissues in adult rat (Canoll et al., 1993, Dev. Brain Res., 75:293–298; Barnea et al., 1993, Mol. Cell. Biol., 13:1497–1506). RPTPβ exists in three forms, one secreted form and two membrane bound forms, that differ by the absence of 860 residues from the spacer domain (Levy et al., 1993, J. Biol. Chem., 268:1053–10582; Maurel et al., 1994, Proc. Natl. Acad. Sci. USA, 91:2512–2516). The secreted form has been identified as a chondroitin sulfate proteoglycan from rat brain called phosphocan (3F8 proteoglycan) (Barnea et al., 1994, Cell, 76:205; Maurel et al., 1994, Proc. Natl. Acad. Sci. USA, 91:2512–2516; Shitara et al., 1994, J. Biol. Chem. 269:20189–20193). The transmembrane form has also been shown to be expressed in a form of a chondroitin sulfate proteoglycan (Barnea et al., 1994, J. Biol. Chem., 269:14349–14352). Purified phosphocan can interact in vitro with the extracellular matrix protein tenascin, and with the adhesion molecules, N-CAM and Ng-CAM (Barnea et al., 1994, J. Biol. Chem., 269:14349–14352; Grumet et al., 1993, J. Cell. Biol., 120:815–824; Grumet et al., 1994, J. Biol. Chem., 269:12142–12146; Milev et al., 1994, J. Cell. Biol., 127:2512–2516). The experiments of the examples described infra were conducted to identify functional ligands for RPTPβ.

3. SUMMARY OF THE INVENTION

The invention relates to the identification and use of compounds to treat neurologic diseases including those characterized by insufficient, aberrant, or excessive neurite growth, differentiation or survival. The invention is based, in part, on the discovery that the CAH domain of RPTPβ (RPTPβ-CAH) is the ligand for contactin and that its binding results in neurite growth, differentiation and survival. More specifically, the invention relates to the identification and use of compounds that mimic, enhance or suppress the effects of RPTPβ-CAH on neurite growth, differentiation and survival. The invention further relates to assays for identifying such compounds.

In the examples described infra, it is shown that receptor phosphatase RPTPβ, specifically interacts with two ligands, one on the surface of glial cells, and the other on the surface of neuronal cells. Using expression cloning in COS7 cells and bioaffinity purification, the neuronal ligand was identified to be the rat homologue of the cell recognition molecule contactin (F11/F3). Using combinations of soluble and membrane bound forms of RPTPβ and contactin it is demonstrated that the reciprocal interaction between the two molecules is mediated by the CAH domain of the phosphatase. Moreover, it is found that when used as a substrate, the CAH domain of RPTPβ induced neurite growth, differentiation and survival of primary neurons and IMR-32 neuroblastoma cells. Finally, using antibody perturbation experiments, the contactin ligand was found to be a neuronal receptor for the CAH domain of RPTPβ. The data indicate that the interactions between contactin, a cell recognition molecule, and RPTBβ, a transmembrane protein tyrosine phosphatase, plays an important role in neuronal development and differentiation.

3.1. DEFINITIONS

As used herein, the following terms and abbreviations shall have the meanings indicated below:

| | |
|---|---|
| base pair(s) | bp |
| carbonic anhydrase | CAH |
| carbonic anhydrase domain of RPTPβ | RPTPβ |
| complementary DNA | cDNA |
| counts per minute | cpm |
| deoxyribonucleic acid | DNA |
| fibronectin type III | FNIII |
| glycosyl-phosphatedylinositol | GPI |
| kilobase pairs | kb |
| kilodation | kDa |
| micrograms | μg |
| micrometer | μm |
| nanograms | ng |
| nanometer | nm |
| nucleotide | nt |
| phospholipdase C | PI-PLC |
| polyacrylamide gel electrophoresis | PAGE |
| polymerase chain reaction | PCR |
| receptor type tyrosine phosphstase beta | RPTPβ |
| ribonucleic acid | RNA |
| sodium dodecyl sulfate | SDS |
| units | u |

4. DESCRIPTION OF THE DRAWINGS

FIGS. 1A–1C. DETECTION OF A MEMBRANE BOUND LIGAND FOR RPTPβ.

FIG. 1A. Schematic presentation of RPTPβ and the different subdomains used to construct fusion proteins with human IgG1-Fc, (CAH—Carbonic anhydrase-like domain, FN—Fibronectin type III repeat, M—plasma membrane).

Figure 1B:
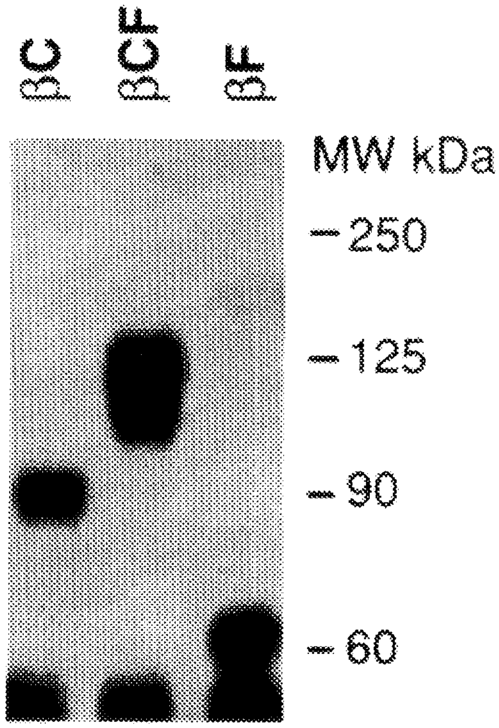
Figure 1D:
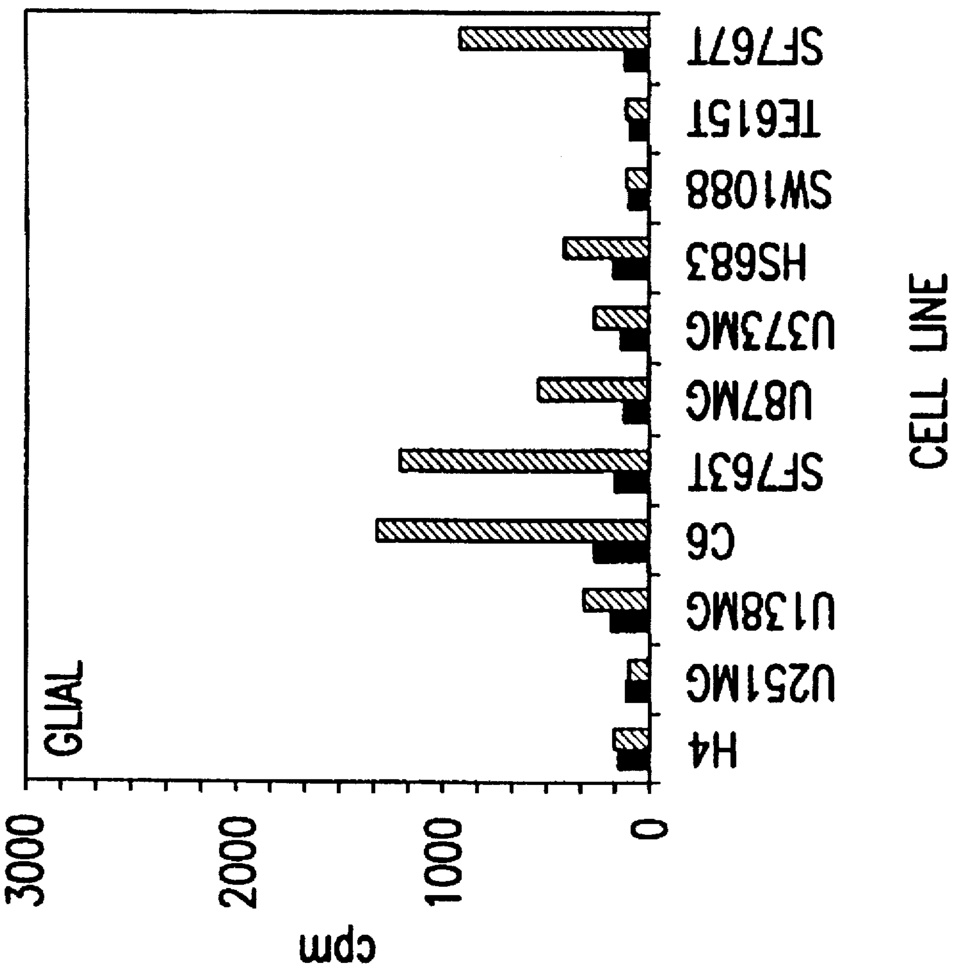

FIG. 1B. Expression of the chimeric IgG-Fc molecules. Different β-Fc fusion proteins containing the CAH or the FN domains (βC and βF respectively) or both domains (βCF) were purified from 293 cells medium on Sepharose Protein A columns. These proteins were separated on SDS gel under reducing conditions, transferred to nitrocellulose membranes and immunobloted with antibodies against human IgG.

Figure 1C:
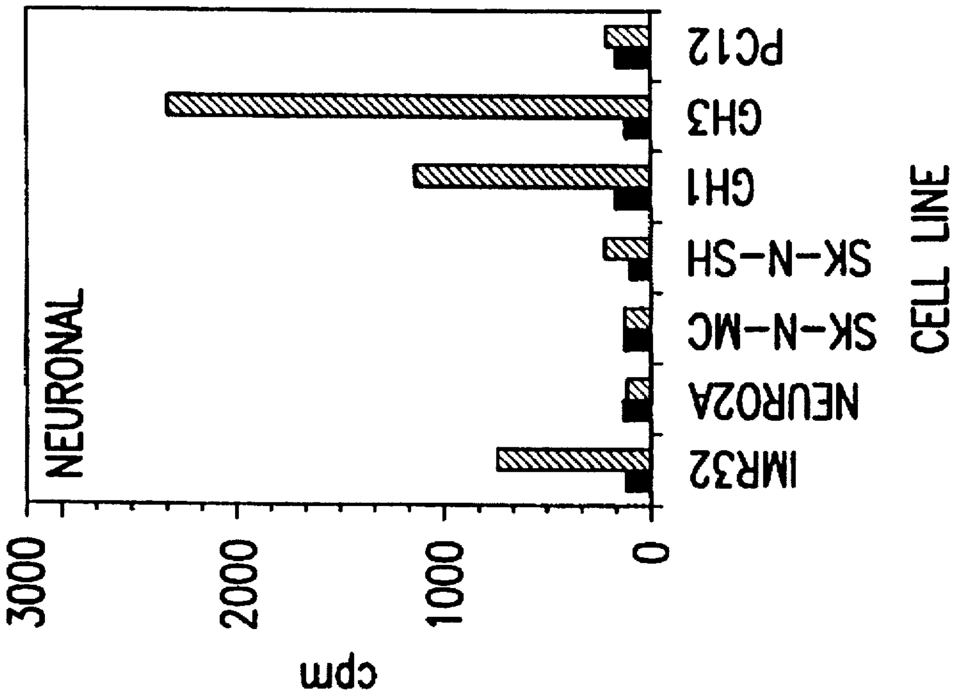

FIG. 1C. Binding of βCF to cell line derived from neuronal (neuroblastoma and neuroendocrine) and glial (glioblastoma and astrocytoma) tumors. Cells were incubated with control medium (none; filled rectangles) or with medium containing βCF-Fc fusion protein at 0.4 mg/ml (βCF; hatched rectangles). After washing, bound βCF was detected by further incubation with $[I^{125}]$-Protein A as described in the Materials and Methods subsections in the examples.

Figure 2A:
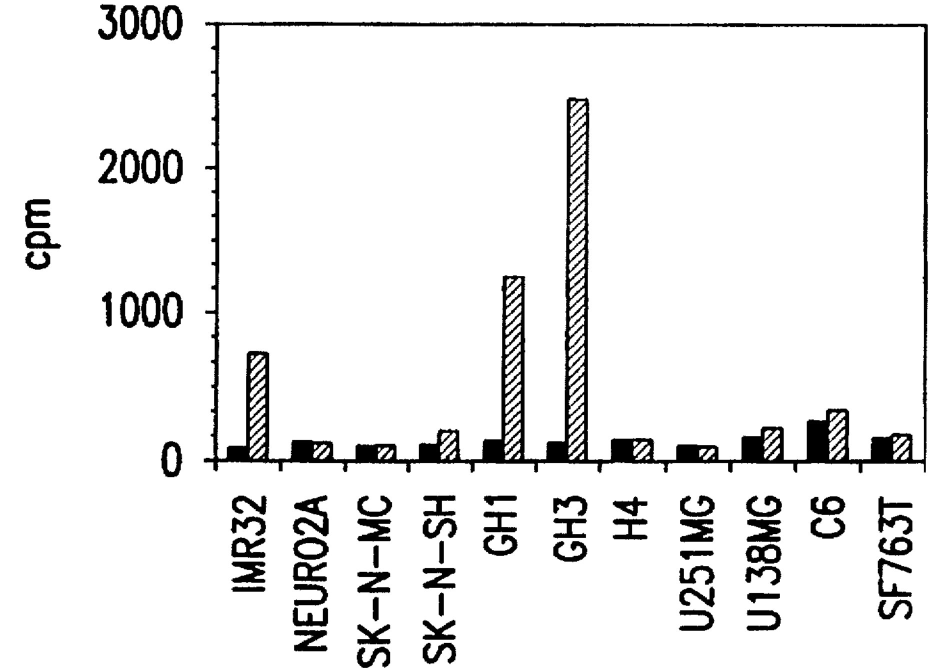
Figure 2C:
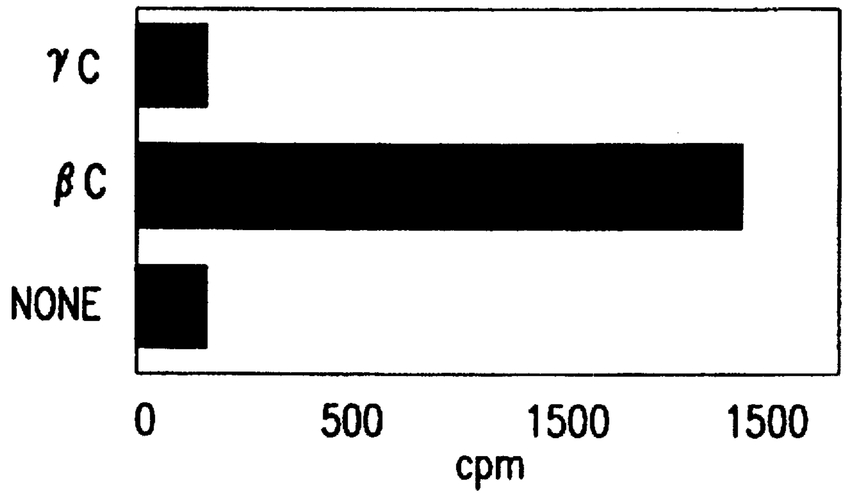
Figure 2B:
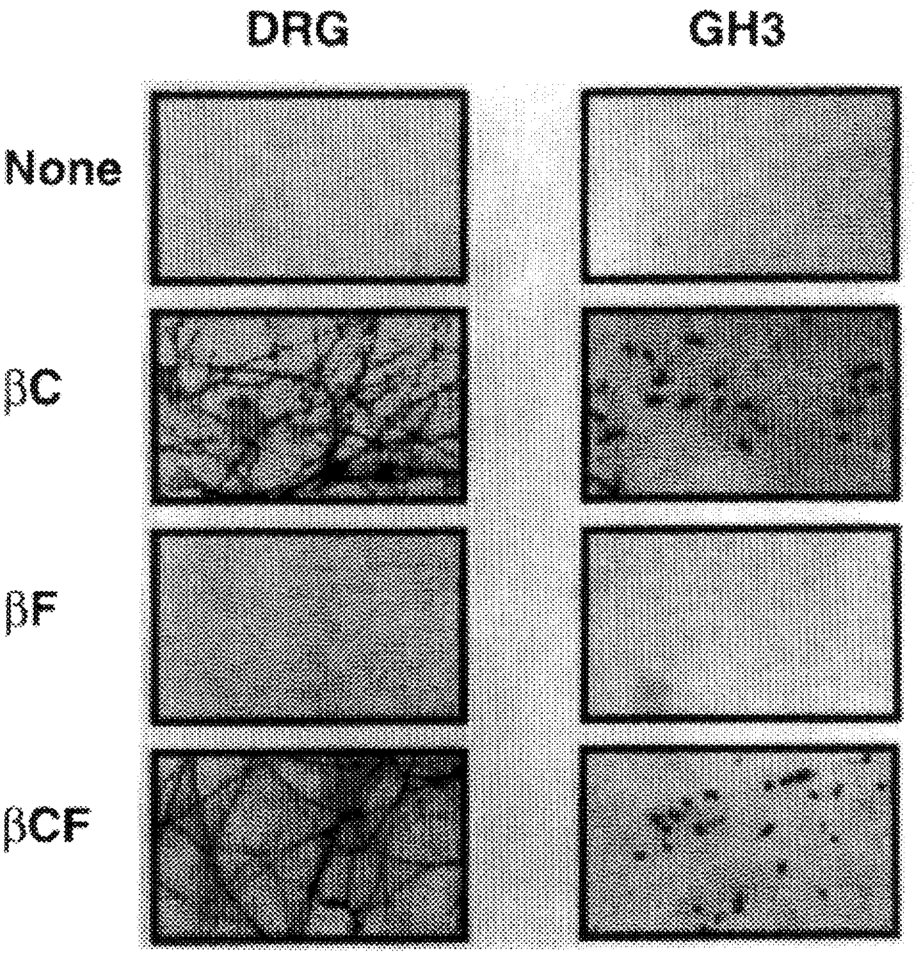

FIGS. 2A–C. SPECIFIC BINDING OF THE CARBONIC ANHYDRASE-LIKE DOMAIN OF RPTPβ (βC) TO NEURONS AND NEURONAL CELL LINES

FIG. 2A. Binding of (βC) to neuronal and glial tumors derived cell lines. Medium control (none; filled rectangles) or medium containing βC-Fc fusion protein at 0.25 ug/Ml were used (βC; hatched rectangles). Bound fusion proteins were detected following incubation with $[I^{125}]$-Protein A.

FIG. 2B. Binding of the different subdomains of RPTPβ to GH3 cells and to primary neurons. GH3 cells and primary cultures of rat dorsal root ganglia (DRG) were incubated with control medium (None) or medium containing Fc fusion proteins with the CAH domain (βC), the FN domain (βF) or both domains (βCF) for 1 hour at RT. Unbound proteins were removed and the bound Fc-fusion proteins were visualized by immunostaining using biotinylated anti human IgG antibodies and streptavidin alkaline phosphatase as described in the Materials and Methods subsections in the examples.

FIG. 2C. Fc fusion proteins containing the CAH domains of RPTPβ (βC) or RPTPγ (γC) were use in binding assay to GH3 cells. Binding was performed as described in A. The results are expressed as means of three experiments.

FIG. 3. COVALENT CROSS LINKING OF βC TO ITS MEMBRANE BOUND LIGAND

Fc-fusion proteins containing the CAH (C) or the FN domains (F) of RPTPβ were allow to bind to $(^{35}S]$-methionine labeled IMR-32 neuroblastoma cells (IMR), GH3 pituitary tumor cells or COS7 cells as indicated. Following one hour incubation, unbound proteins were washed away and 1 mM of the reversible cross linker (DSSTP) was added for additional 30 minutes at 4° C. Cell lysates were prepared and the cross linked proteins were precipitated using Sepharose protein A as detailed in the Materials and Methods subsections of the examples. The proteins were resolved on 8–16% SDS gels under reducing conditions followed by autoradiography (under these conditions the crosslinker is cleaved). Sizes of molecular mass marker proteins are indicated in kilodaltons.

FIGS. 4A–C. EXPRESSION CLONING OF RAT CONTACTIN, THE βC-LIGAND IN GH3 CELLS

Figure 4A:
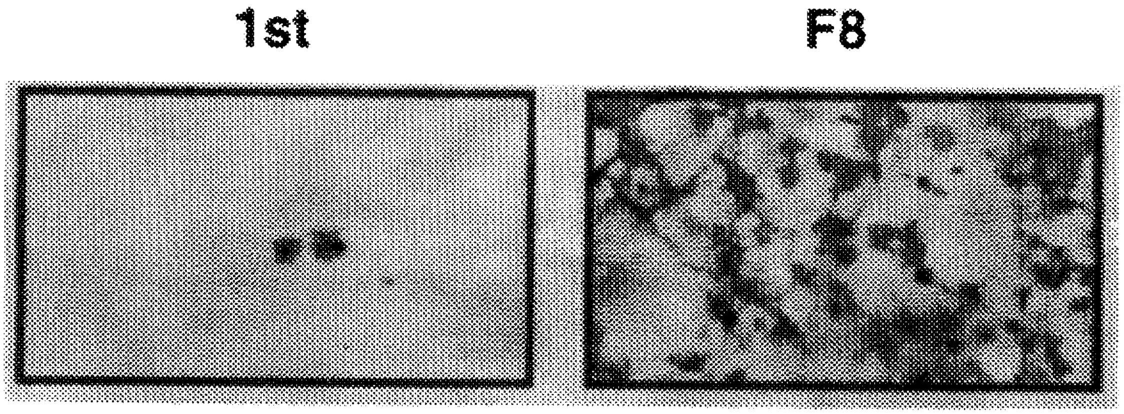

FIG. 4A. Screening of GH3 expression library in COS cells. COS7 cells were transfected with a cDNA pool consist of 3000 independent clones (1st—round of screening) or with clone F8 that was isolated after the fifth screening round (F8). After 72 hours cells were incubated for one hour with medium containing βCF-Fc. Unbound Fc-fusion proteins were removed and the cells were fixed and immunostained using biotinylated anti-human IgG antibodies followed by streptavidin alkaline phosphatase and NBT/BCIP as substrate. Cells were photographed using a bright field microscope.

FIG. 4B. Sequence of βC-ligand (SEQ ID No:2). The deduced amino acid sequence of the F8 cDNA clone encoding the βC-ligand. The hydrophobic C and N-terminal sequences are underlined, and the amino acid sequences obtained from a purified protein by receptor bioaffinity chromatography are boxed. Residues that are different from human contactin are shown below.

Figure 4C:
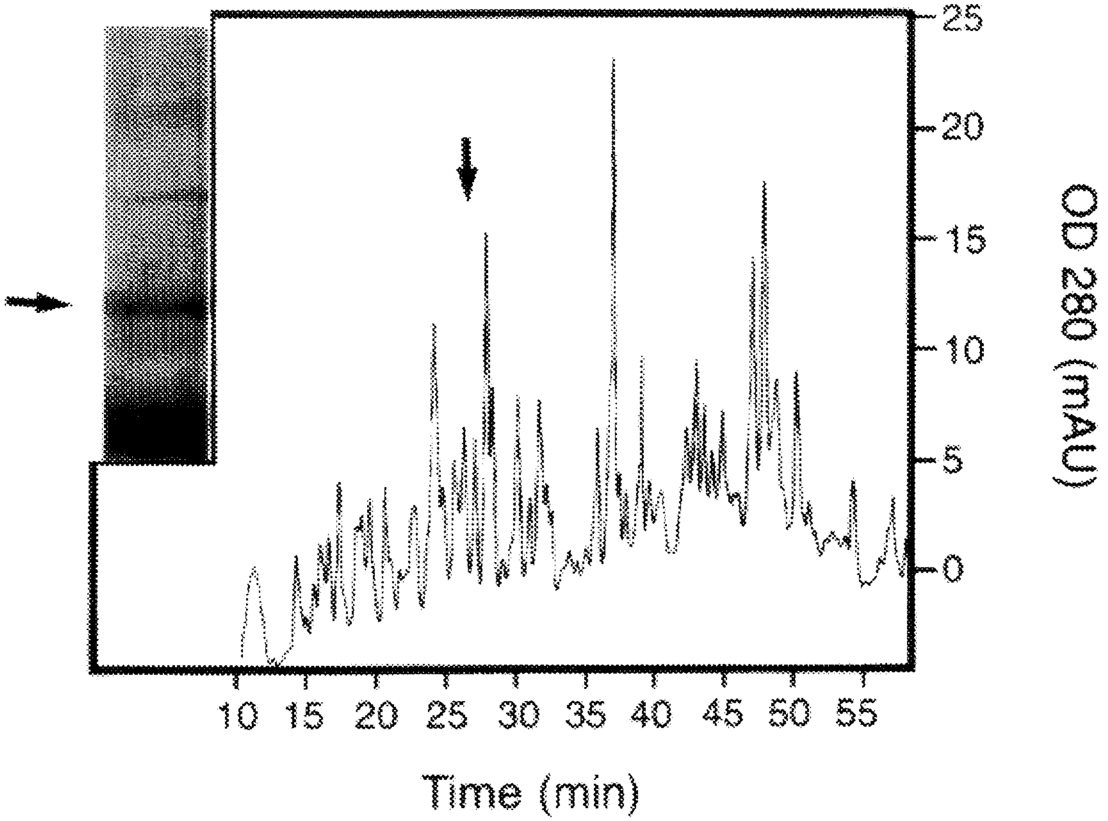

FIG. 4C. Bioaffinity purification of βC-ligand from GH3 cells. βC-ligand was purified from solubilized GH3 membranes using βCF-FC column as described in the Materials and Methods subsections of the examples. Eluted proteins were loaded on 7.5% SDS gel, transferred to ProBlott membranes and stained with coomassie blue. The stained membrane is shown along with molecular marker proteins. One quarter of the 140 kDa band was exposed and used for determination of the N-terminal sequence. The remaining material was digested with trypsin and loaded on Reliasil C-18 column. The HPLC profile is shown and the peptide used for microsequencing is marked by an arrow. The sequences obtained are identical to those that are boxed in FIG. 4*b*.

Figure 5A:
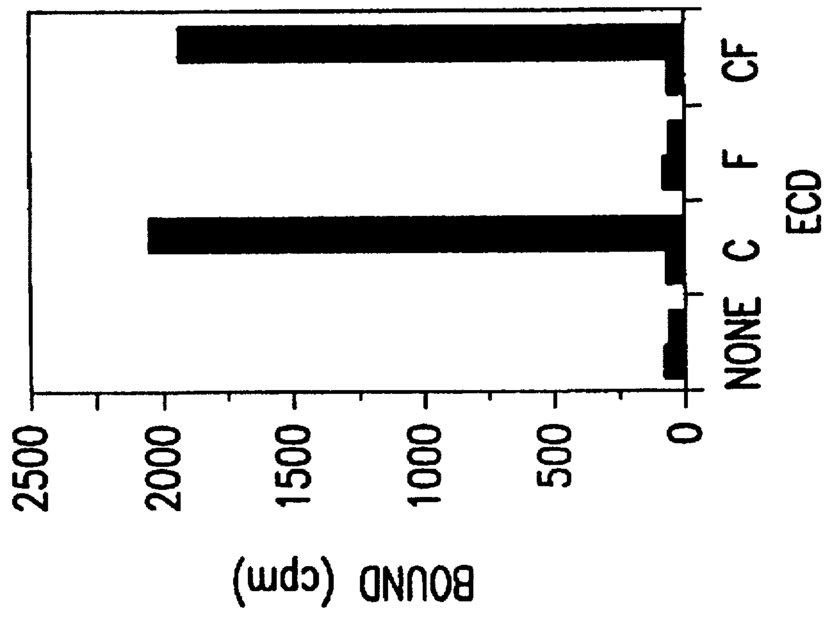
Figure 5B:
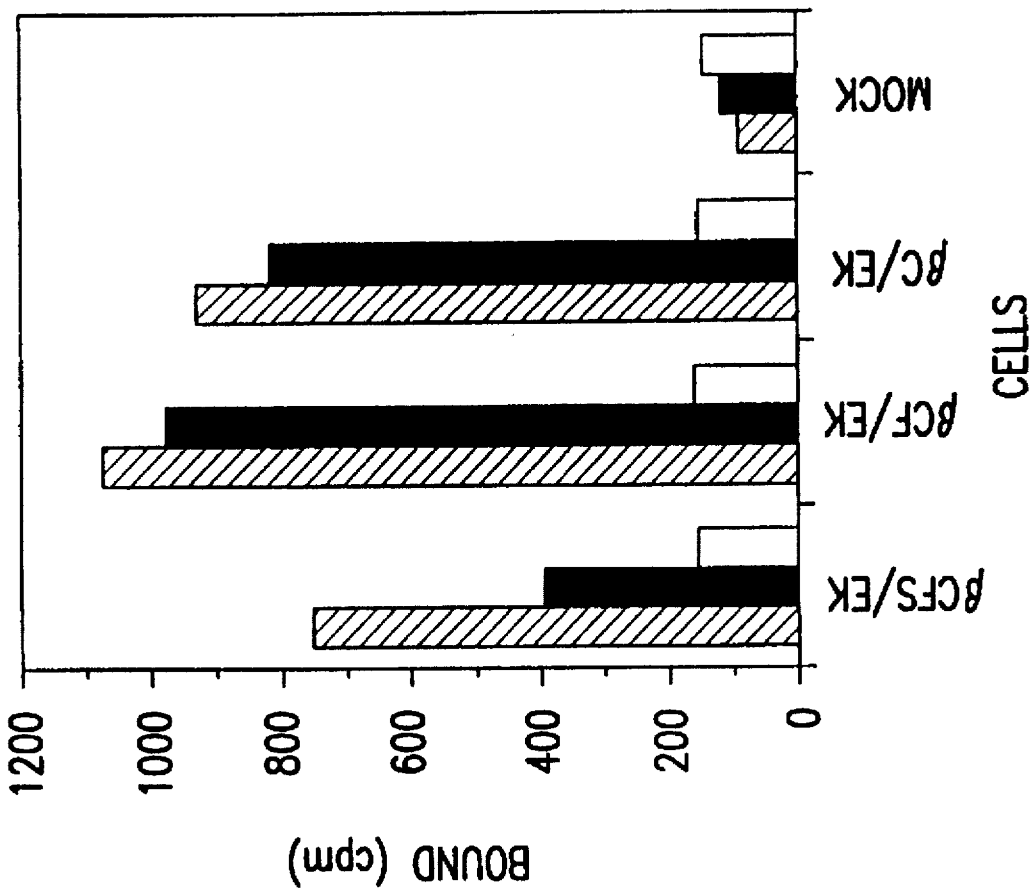

FIGS. 5A–B. BINDING OF SOLUBLE RPTPβ FORMS TO CONTACTIN AND BINDING OF SOLUBLE CONTACTIN FORM TO RPTPβ

FIG. 5A. Binding specificity subdomains of RPTPβ to contactin expressing cells. COS cells were transfected with clone F8 encoding wild type contactin (hatched bars) or with β-Gal expressing plasmid as a control (filled bars). Cells were analyzed for their ability to bind Fc-fusion proteins containing the CAH domain (C), the FN III domain (F) or both domains (Fc).

FIG. 5B. Binding of human contactin Fc-fusion protein to cells expressing PRTPβ/EGF-R chimeric receptors. COS cells were transfected with chimeric molecules in which the extracellular region of the short form of RPTPβ (βCFS/EK), the CAH and the FNIII domains (βCF/EK) or the CAH domain alone (βC/EK) were fused to the transmembrane and cytoplasmic domains of EGF receptor. Binding of the contactin-Fc fusion protein (hatched bars) or control Fc-fusion (black bars) were carried on after 72 hours as described in A. The expression level of the chimeric receptors was determined using antibodies against the extracellular domain of human RPTPβ (shaded bars) as described in Experimental Procedures.

FIGS. 6A–C. EFFECT OF PI-PLC TREATMENT ON THE INTERACTION OF βC WITH CONTACTIN

Figure 6A:
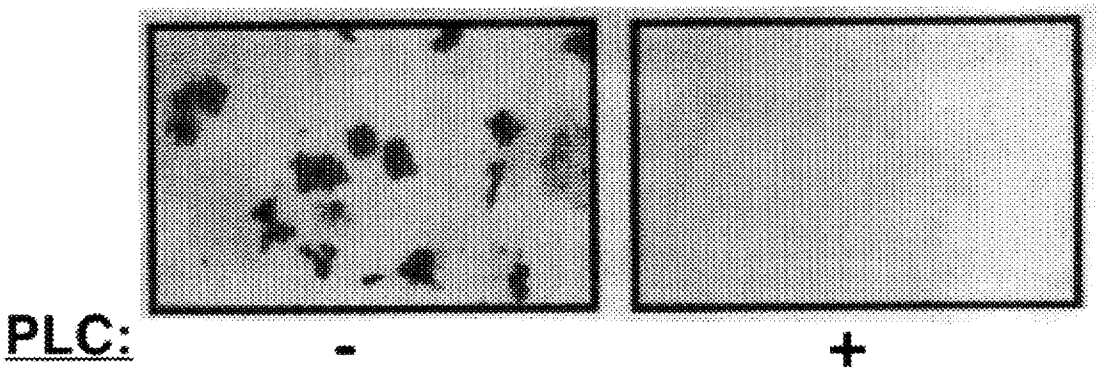

FIG. 6A. COS cells were transfected with clone F8 and 72 hours later they were treated with (+) or without (−) PI-PLC (400 mU). Cells were incubated with βCF-FC and positive cells detected as described in the legend to FIG. 4.

Figure 6B:
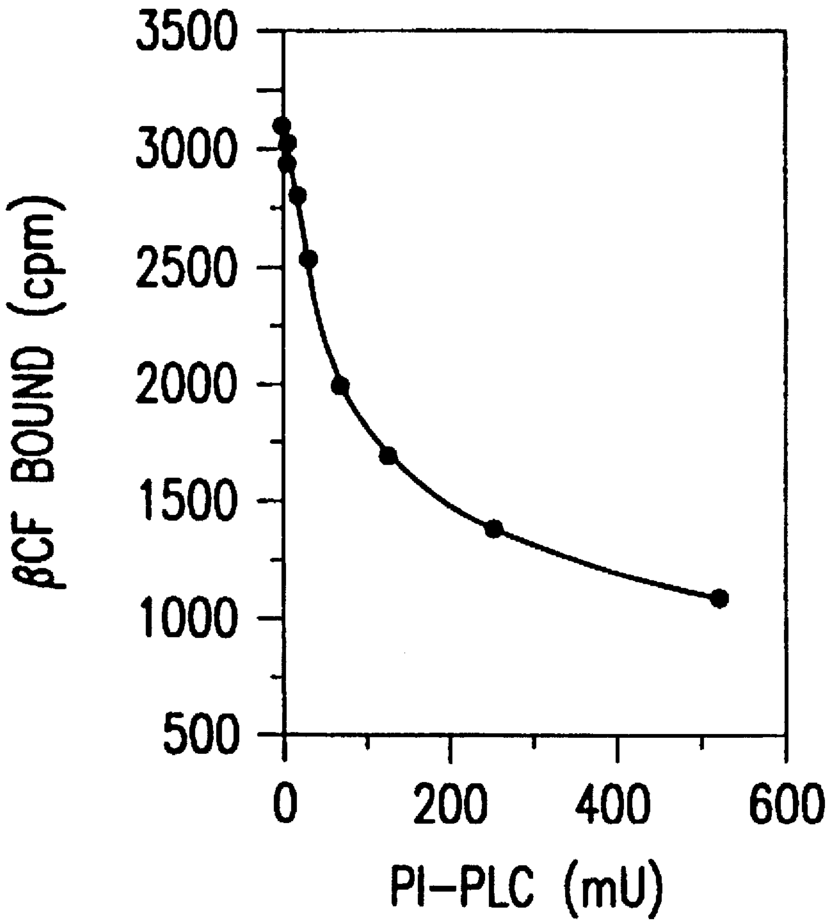

FIG. 6B. GH3 cells were treated with increasing amounts of PI-PLC as indicated and then incubated with medium containing βCF-Fc at 0.4 mg/ml for one hour. After extensive washing cell bound proteins were detected by further incubation with $[I^{125}]$ Protein A.

Figure 6C:
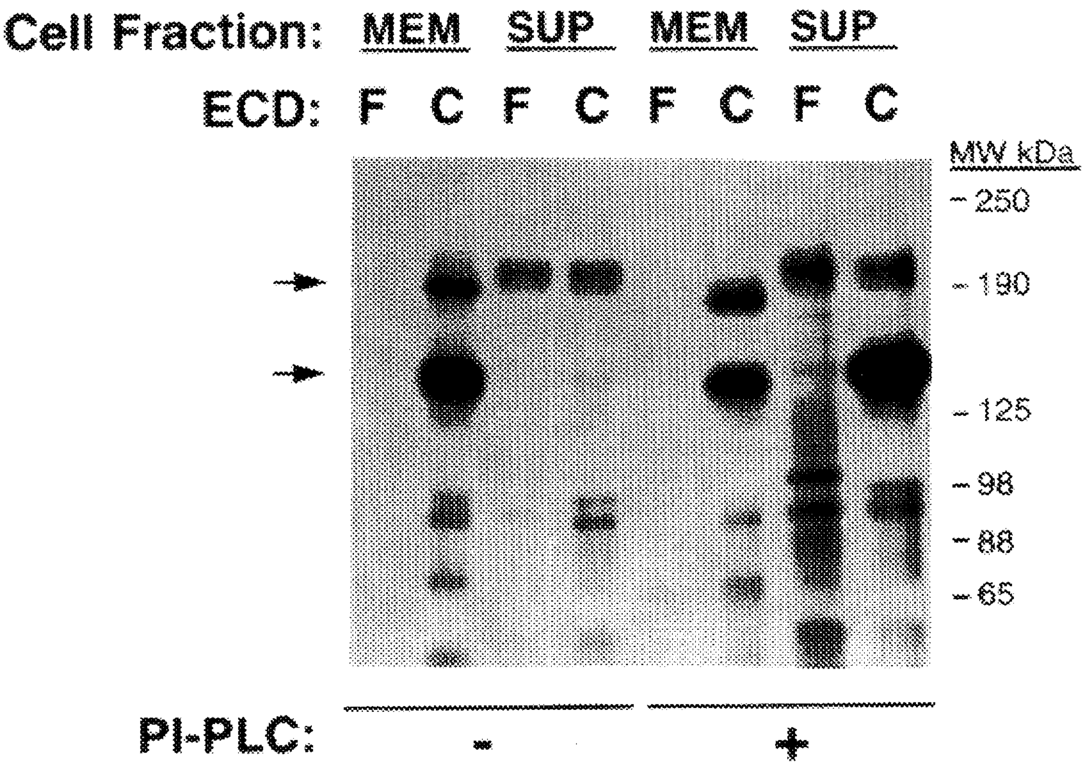

FIG. 6C. GH3 cells were metabolically labeled with $[^{35}S]$-methionine and treated with or without PI-PLC as indicated at the bottom. Cell supernatants (SUP) and solubilized cell membranes (MEM) were subjected to receptor bioaffinity precipitation using Fc fusion proteins containing the carbonic anhydrase domain (C) or the fibronectin type III repeat (F) of RPTPβ. The washed complexes were separated on a 7.5% SDS gel under reducing conditions. Autoradiogram of the fixed and dried gel is shown along with the location of molecular weight marker proteins. The 140 kDa band of contactin and the coprecipitated 180 kDa protein are indicated by arrows.

FIGS. 7A–B. BIOLOGICAL EFFECT OF RPTPβ CAH DOMAIN ON NEURITE GROWTH

Figure 7A:
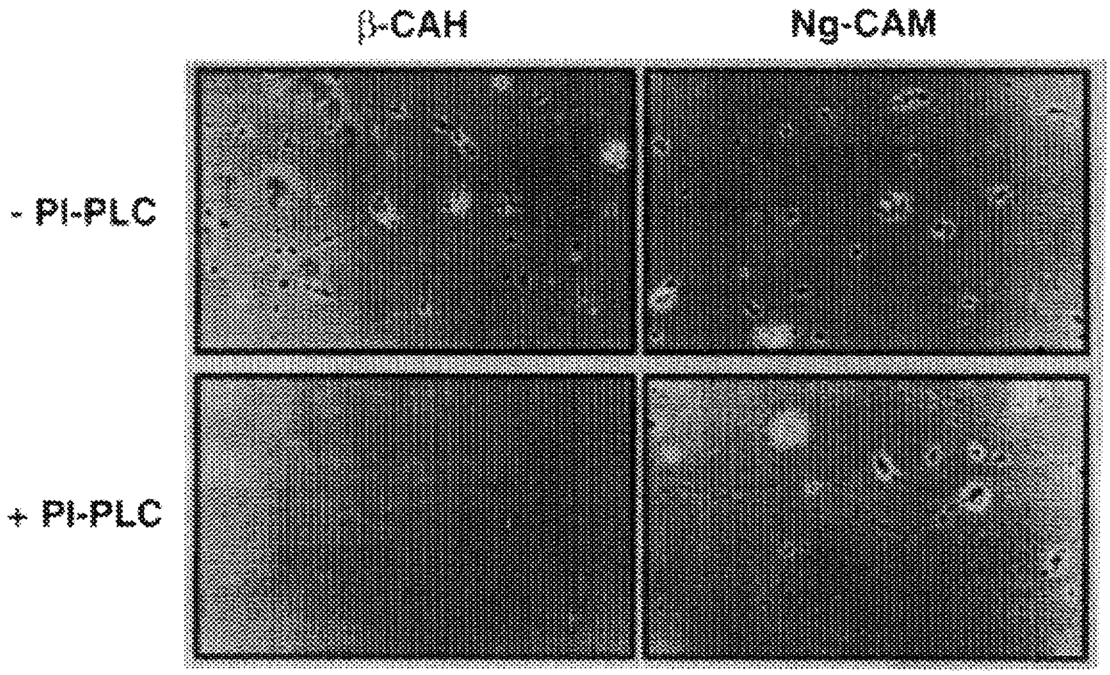

FIG. 7A. Effect of PI-PLC on neurite growth of chick neurons on the CAH domain of RPTPβ. Primary tectal cells were treated with or without PI-PLC as indicated for one hour and plated on βC-FC or Ng-CAM coated dishes. After 24 hours, unbound cells were removed by gentle wash and the plate was fixed and photographed.

Figure 7B:
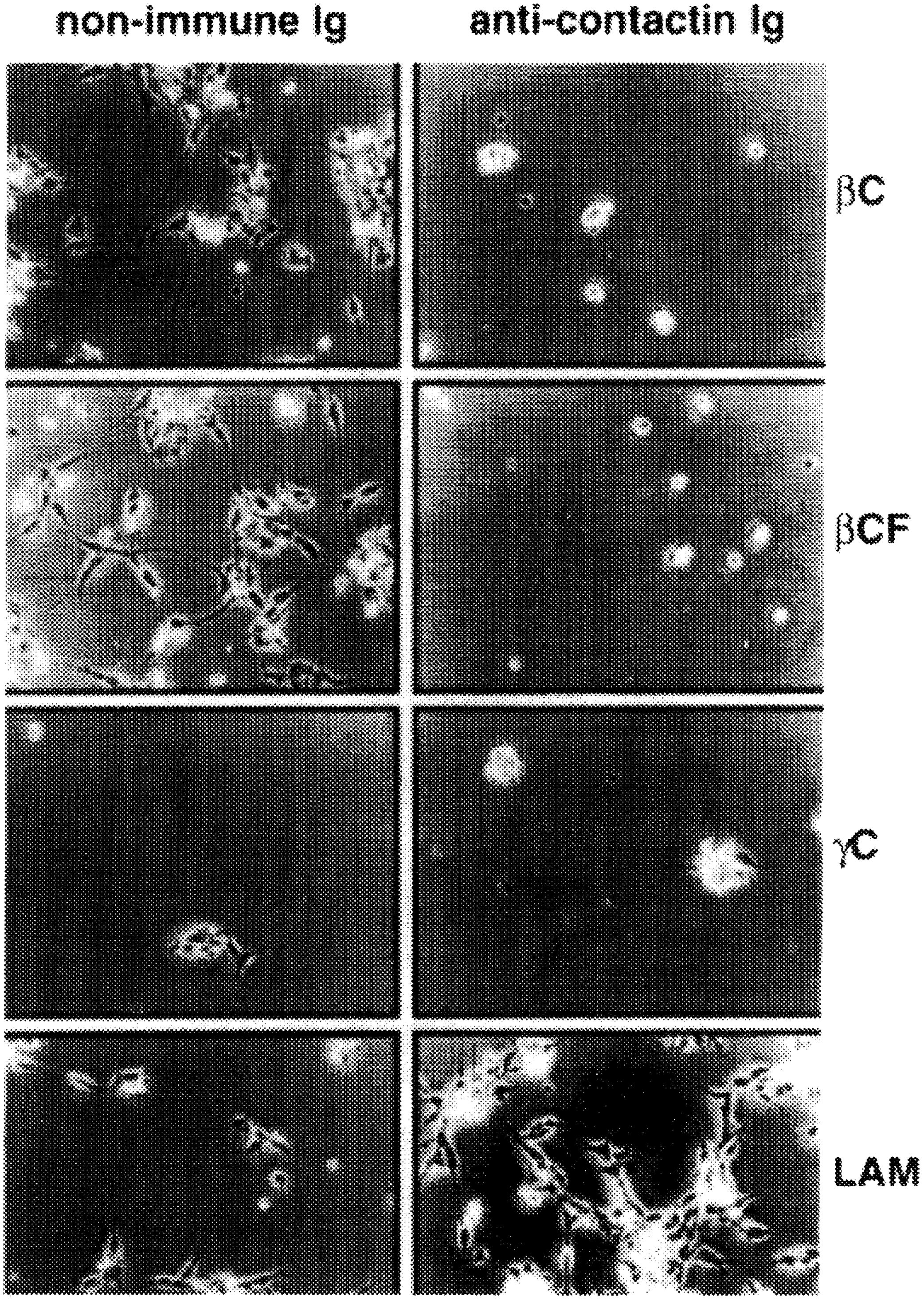

FIG. 7B. Process extension of IMR32 cells induced by βC and βCF-Fc fusion proteins is inhibited by antibodies against contactin. Petri dishes were coated in a circular array with 2 μl drops of Fc fusion proteins (βC, βCF and γC) or with laminin (Lm). After removing the unabsorbed proteins, the dishes were blocked with BSA and IMR32 were allowed to adhere to the dishes for 3 h. Then the medium was removed and replaced with fresh medium containing non-immune or anti-contactin Ig as indicated, at a final concentration of 250 μg/ml. The culture were incubated for 48 h, fixed and photographed under 200×magnification as described in the Materials and Methods subsections in the EXAMPLES.

5. DETAILED DESCRIPTION OF THE INVENTION

A large group of protein tyrosine phosphatases have structural characteristics suggesting that they function as cell surface receptors. Receptor type tyrosine phosphatase β (RPTPβ) is expressed in the developing nervous system and it contains a carbonic anhydrase (CAH) domain as well as a fibronectin type III (FNIII) repeat in its extracellular domain. A variety of experiments were conducted to search for ligands of RPTPβ. These experiments led to the surprising recognition that the CAH domain of RPTPβ is a functional ligand for contactin, a GPI-membrane anchored neuronal cell recognition molecule that functions as a receptor on neurons. The CAH domain of RPTPβ (RPTPβ-CAH) induces cell adhesion and neurite growth of primary tectal neurons, and differentiation of neuroblastoma cells. The assays of the invention identify compounds that mimic, enhance, or inhibit the contactin mediated effects of RPTPβ-CAH on neural cells including, but not limited to, agonists and antagonists of RPTPβ-CAH. Therapeutic uses of compounds so identified are also provided. The invention is described in detail in the following subsections and examples for purposes of clarity and not by way of limitation.

5.1. BIOLOGY OF THE INTERACTION BETWEEN CONTACTIN AND THE CAH DOMAIN OF RPTPβ

During development of the nervous systems, neurons are guided by secreted and cell bound molecules that provide both negative and positive cues. The experiments described in the examples of Sections 6.1 and 6.2 show that RPTPβ, a receptor type protein tyrosine phosphatase, may provide such a signal by interacting with the axonal recognition molecule contactin. RPTPβ is a developmentally regulated protein that exists in three forms, one secreted and two membrane bound. The extracellular region of RPTPβ has a multidomain structure consisting of a CAH-like domain, a single FNIII repeat, and a long cysteine free spacer region. The complex structural nature of its extracellular region may result in a multifunctional protein that is able to interact with different proteins. As documented by the data shown herein, the CAH and the FNIII domains bind to at least two potential ligands present on neurons or glial cells. Functional expression cloning in COS7 cells and affinity purification with a specific affinity matrix followed by microsequencing enabled unequivocal identification of the cell recognition molecule contactin (F3/F11) as a neuronal ligand of RPTPβ. The interaction between contactin and RPTPβ is mediated via the CAH domain of the phosphatase, while the FNIII domain appears to bind to another molecule expressed on the surface of glial cells. It was previously shown that the secreted proteoglycan form of RPTPβ interacts with tenascin, N-CAM and Ng-CAM (Grumet et al., 1994, J. Biol. Chem., 269:12142–12146; Barnea et al., 1994, J. Biol. Chem., 269:14349–14352; Grumet et al., 1993, J. Cell. Biol., 120:815–724; Milev et al., 1994, J. Cell. Biol., 127:1703–1715). Since N-CAM and Ng-CAM do not bind directly to the CAH or the FNIII domain of RPTPβ, they may interact with the large spacer domain of the phosphatase. Alternatively, they could interact with RPTPβ through a third component. Contactin may fulfill this function since it has been shown to interact with Ng-CAM, Nr-CAM, and the matrix proteins tenascin and restriction (Brümmendorf et al., 1993, Neuron, 10:711–727; Morales et al., 1993, Neuron, 11:1113–1122; Zisch et al., 1992, J. Cell. Biol., 119:203–213). The various subdomains of the extracellular region of RPTPβ are able to interact with several distinct proteins that are expressed on diverse cell types in the central nervous system.

In contrast to other cell recognition molecules that are widely expressed in the nervous system, members of the contactin subgroup appear to be expressed in a restricted manner on specific axons during development (Dodd et al., 1988, Neuron, 1:105–116; Faivre-Sarrailh et al., 1992, J. Neurosci., 12:257–267). The spatial and temporal expression pattern of these proteins indicates they play an important role during development of the nervous system. Contactin was found to be exclusively expressed on neurons during development in fiber-rich areas of the retina, tectum, spinal cord and cerebellum (Ranscht, 1988, J. Cell. Biol. 107:1561–1573). It was found to be localized in the postnatal and adult mouse cerebellum in axonal extensions of the granule cells in the parallel layer (Faivre-Sarrailh et al., 1992, J. Neurosci., 12:257–267). This pattern of expression is overlapping with the expression pattern of RPTPβin the rat. RPTPβwas shown to be expressed in fiber-rich regions such as the parallel fibers of the cerebellum and the spinal cord (Canoll et al., 1993, Dev. Brain Res., 75:293–298; Milev et al., 1994, J. Cell. Biol., 127:1703–1715). RPTPβ is also expressed on glial and radial glial cells, and its secreted form is produced by astrocytes. Therefore, both forms of RPTPβ may modulate neuronal function via interactions with contactin.

The contactin subgroup of glycoproteins all share structural similarity in that they are, glycosyl-phosphatidylinositol (GPI)-anchored proteins. They also exist in soluble forms generated as a result of membrane release or by expression of alternative spliced forms (Br ümmendorf and Rathjen, 1993, J. Neurochem., 61:1207–1219). Differential expression of the membrane-bound and soluble forms of contactin was found in the hypothalamus-hypophyseal system (Rougon et al., 1994, Braz. J. Med. Biol. Res., 2:409–414). RPTPβ also exists in either membrane bound or secreted forms that are developmentally regulated. Therefore, both RPTPβand contactin may act as either a ligand or a receptor for each other. Hence, the classical notion of ligand receptor interaction does not fully explain this system since both components might switch roles at different stages of development. For example, the soluble form of RPTPβ produced by glial cells may act as a ligand for the membrane bound form of contactin expressed on the surface of neuronal cells. Conversely, the soluble form of contactin may act as ligand for the membrane bound form of RPTPβ expressed on the surface of glial cells. Moreover, interaction between the membrane bound forms of contactin expressed on the surface of neurons with the membrane form of RPTPβ expressed on the surface of glial cells may lead to bidirectional signals between these two cell types. Such complex interactions between the various forms of RPTPβ and contactin may generate developmentally regulated unidirectional and bidirectional signals.

While not being limited to any theory or explanation of how the invention works, the following is hypothesized to explain how the CAH domain of RPTBβ binds to contactin. Carbonic anhydrases are highly efficient enzymes that catalyze the hydration of $CO_2$. Yet, the CAH domain of PTPases were not thought to be endowed with enzymatic activity due to substitution of two of the three key histidine residues that are essential for enzymatic activity (Barnea et al., 1993, Mol. Cell. Biol., 13:1497–1506). In contradistinction, the highly packed hydrophobic core as well as the hydrophobic residues that are exposed on the surface of carbonic anhydrase structure and which are conserved in the CAH domains of RPTPγ and β may be involved in protein-protein interaction and thus function as a ligand binding domain (Barnea et al., 1993, Mol. Cell. Biol., 13:1497–1506). It is of note that Vaccinia virus contains a transmembrane protein with a CAH-like domain in its extracellular domain, which was thought to be involved in binding of the virion to host proteins (Maa et al., 1990, J. Biol. Chem., 265: 1669–1577). Therefore, in theory but not by way of limitation, compounds exhibiting effects which mimic, enhance, or inhibit the contactin mediated effects of RPTPβ-CAH on neuronal cells may do so via other members of the contactin family of glycoproteins, and may do so even if lacking in CAH activity.

A number of models may be proposed for how contactin, a GPI-linked protein that is inserted into the outer leaflet of the plasma membrane, transmits a signal into the cells to promote neurite outgrowth. In theory, and not by way of limitation, one possibility is that contactin is able to interact with a transmembrane signaling component. The p180 protein that was coprecipitated with contactin is a candidate for such a signaling protein (FIG. 6C). p180 may be membrane-associated since it may not be released by phospholipase C treatment. Another potential signal transducer may be L1/Ng-CAM or a related molecule. This transmembrane CAM was shown to interact with contactin (Brümmendorf et al., 1993, Neuron, 10:711–727), and to initiate second messenger cascade via its cytoplasmic domain (Doherty and Walsh, 1994, Curr. Opin. Neurobiol., 4:49–55). The best characterized GPI linked signaling protein is the ciliary neurotrophic factor receptor (CNTF receptor). Following ligand binding, the CNTFR interacts with the signal transducer gp130. The gp130 protein that is shared by several lymphokines and cytokines such as IL-6, LIF and Oncostatin, undergoes dimerization followed by recruitment of the cytoplasmic Jak protein tyrosine kinases. Stimulation of the Jak kinases leads to activation of both the Ras/MAP kinase and the Stat signaling pathways that relay signals from the cell surface to the nucleus. A contactin associated protein such as p180 may have a function similar to the function of gp130.

As demonstrated by the examples infra, the binding of the CAH domain of RPTPβ to contactin leads to cell adhesion and neurite outgrowth. It seems unlikely that the induction of neurite growth is a default response resulting from cell adhesion per se. Neurons were found to adhere to extracellular matrix proteins such as tenascin and restriction in short term binding assays, but these substrates did not promote further neurite extension (Schachner et al., 1994, Perspect. Dev. Neurobiol., 1:33–41). It was recently reported that the FNIII domain of contactin is responsible for adhesion, while the neurite promoting activity was attributed to the Ig domains (Durbec et al., 1994, Eur. J. Neuro., 6:461–472). Another study demonstrated that contactin can mediate the repulsion of neurons by restriction (Pesheva et al., 1993, Neuron, 10:69–82). Again, this effect was proposed to occur in a stepwise manner, first an adhesion step that was followed by a signal that was transduced to the cells leading to retraction. Therefore, in light of the results presented herein, it may be that in response to different stimuli, the same molecule can transmit opposite signals depending on the context or milieu. Whatever the mechanism, the results presented here demonstrate that a receptor type tyrosine phosphatase serves as a functional ligand for a GPI-anchored cell adhesion molecule.

Contactin may also serve as a functional ligand for RPTPβ. Modulation of phosphatase activity by neuronal contactin may result in signaling to glial cells. If this does occur, this kind of bidirectional flow of information should allow the interacting cells to respond quickly to local environmental changes during development. Two other receptor type tyrosine phosphatases RPTPμ and RPTPκ were shown to mediate cell-cell interaction in a hemophilic manner (Brady-Kalany et al., 1993, J. Cell. Biol., 122:961–972; Gebbink et al., 1993, J. Biol. Chem., 268:16101–16104; Sap et al., 1994, Mol. Cell. Biol., 14:1–9). However, changes in catalytic activity as a result of these interactions could not be detected. These phosphatases are joining a growing family of proteins that are involved in cellular recognition that contain intrinsic enzymatic activities, including kinases (Dtrk; Pulido et al., 1992), EMBO J., 11:391–404, β subunit of $Na^+$, $K^+$-ATPase (AMOG; Gloor et al., 1990, J. Cell. Biol., 109:755–788), and β subunit of prolyl 4-hydroxylase (cognin; Rao and Hausman, 1993, Proc. Natl. Acad. Sci. USA, 90:2950–2954).

In summary, the experiments and data described herein demonstrate that RPTPβ is a functional ligand for the GPI-anchored cell recognition molecule contactin. The interactions between these two proteins is mediated by the CAH domain of the phosphatase. In addition, the FNIII of RPTPβ repeat is required for interaction with glia cells, demonstrating that the multidomain structure of RPTPβ enables interactions with different proteins, and indicates that other potential ligands may modulate these interactions.

5.2. SCREENING METHODS AND ASSAYS

The methods and assays of the invention can be used to identify compounds that enhance, mimic, or inhibit the contactin mediated effects of RPTPβ-CAH on neuronal cells. Such compounds include those which act directly at the site of interaction between the CAH domain of RPTPβ and contactin, and those which act downstream in the intracellular signal transduction pathway which stems from that interaction. In addition, such compounds include peptides and polypeptides as well as small organic and inorganic molecules.

The methods and assays of the invention involve exposing contactin expressing neural cells to RPTPβ-CAH in the presence and absence of a test compound. It is shown that the exposure of such cells to RPTPβ-CAH alone will induce contactin mediated cell adhesion, outgrowth, differentiation, survival and neurite extension. Comparison of the results obtained when the cells are exposed to RPTPβ-CAH alone with the results obtained when exposed to RPTPβ-CAH and the test compound reveals those test compounds which enhance, mimic, or inhibit the contactin mediated neural survival, differentiation and growth. Enhancer compounds will cause the effects of RPTPβ-CAH to increase while inhibitor compounds will cause the effects to decrease. Compounds which mimic RPTPβ-CAH will cause the same effects both in the presence and absence of RPTPβ-CAH.

Covalent cross linking will reveal those compounds which are acting at the site of interaction between RPTPβ-CAH and contactin. If such molecules are proteins, they can be isolated and further characterized by expression cloning, affinity purification, and microsequencing.

Treatment of the neural cells with PI-PLC or exposing them to antibodies against contactin will prevent contactin mediated effects. Therefore, those compounds which are acting downstream of the contactin step of the signal transduction pathway are identified by exerting their effects even in the presence of antibodies against contactin or where the cells were subjected to prior treatment with PI-PLC.

A specific embodiment of the methods and assays of the invention is provided below to further illustrate the invention. The scope of the invention is not, however, meant to be limited to the specific details of the embodiment. The materials and methods of this embodiment are set forth more fully in the examples infra.

To analyze the effects of a test compound in accordance with the invention, chick fetal cells, which express contactin on their cell surface are plated on dishes coated with the test compound alone, RPTPβ-CAH and the test compound or RPTPβ-CAH alone, or Ng-CAM as two controls. Those plated on NG-CAM should show no attachment or extension. Those plated on RPTPβ-CAH will show the attachment and neurite extension as in the examples infra. If those plated on RPTPβ-CAH and the test compound, show enhanced or decreased growth and extension as compared with those on RPTPβ-CAH alone, then the test compound enhances or inhibits the contactin mediated effects of RPTPβ-CAH. If those plated on the test compound alone show similar growth to those plated with RPTPβ-CAH alone, then the test compound mimics the contactin mediated effects of RPTPβ-CAH. A similar comparison can be made using the human neuroblastoma cell line IMR-32.

5.3. PEPTIDES THAT MIMIC, ENHANCE, OR INHIBIT THE CONTACTIN MEDIATED EFFECTS OF RPTPβ-CAH ON NEURONAL CELLS

The following peptides corresponding to the CAH domain of RPTPβ and homologues and derivatives thereof may be used in accordance with the invention to mimic, enhance, or inhibit the contactin mediated effects of RPTPβ-CAH on neuronal cells. As used herein, the word modulate shall have its usual meaning, but shall also encompass the meanings of the words enhance, inhibit and mimic. The peptides of the invention correspond to amino acid residues 31 to 300 of RPTPβ (RPTPβ-CAH) and have amino acid sequence (reading from amino to carboxy terminus):

$X_n$
—KLVEEIGWSYTGALNQKNWGKKYPTCNSPKQSPINIDEDLTQVNVNLKKL
—KFQGWDKTSLENTFIHNTGKTVEINLTNDYRVSGGVSEMVFKASKITFHW
—GKCNMSSDGSEHSLEGQKFPLEMQIYCFDADRFSSFEEAVKGKGKLRALS
—ILFEVGTEENLDFKAIIDGVESVSRFGKQAALDPFILLNLLPNSTDKYYI
—YNGSLTSPPCTDTVDWIVFKDTVSISESQLAVFCEVLTMQQSGYVMLMDY
—LQNNFREQQYFSRQVFSSYT
—$Z_n$ (SEQ ID NO:1)

Wherein:

"n" is an integer from 0 to 500;

"X" may represent an amino group, a hydrophobic group, including but not limited to carbobenzoxyl, dansyl, or T-butyloxycarbonyl; an acetyl group; a 9-fluorenylmethoxycarbonyl (FMOC) group; a macromolecular carrier group including but not limited to lipid-fatty acid conjugates, polyethylene glycol, or carbohydrates; and "Z" may represent a carboxyl group; an amido group; a T-butyloxycarbonyl group; a macromolecular carrier group including but not limited to lipid-fatty acid conjugates, polyethylene glycol, or carbohydrates.

In addition to the full-length sequence set forth above, the peptides of the invention may include truncations thereof which mimic, enhance, or inhibit the contactin mediated effects of RPTPβ-CAH on neuronal cells. Such truncated peptides may comprise peptides having at least 3 amino acid residues and which demonstrate the ability to mimic, enhance, or inhibit the contactin mediated effects of RPTPβ-CAH as measured by the methods and assays of the invention as described in Section 5.2.

The peptides of the invention also include analogs of RPTPβ-CAH and of RPTPβ-CAH truncations which may include, but are not limited to, peptides comprising the RPTPβ-CAH sequence, or truncated sequence, containing one or more amino acid substitutions, insertions and/or deletions. Analogs of RPTPβ-CAH homologs, described below, are also within the scope of the invention. The analogs of the invention mimic, enhance, or inhibit the contactin mediated effects of RPTPβ-CAH on neuronal cells, and may, further, possess additional advantageous features, such as, for example, increased bioavailability, and/or stability, or reduced host immune recognition. One possible class of amino acid substitutions would include those amino acid changes which are predicted to stabilize the structure of the peptides of the invention.

Amino acid substitutions may be of a conserved or non-conserved nature. Conserved amino acid substitutions consist of replacing one or more amino acids of the RPTPβ-CAH peptide sequence with amino acids of similar charge, size, and/or hydrophobicity characteristics, such as, for example, a glutamic acid (E) to aspartic acid (D) amino acid substitution. When only conserved substitutions are made, the resulting peptide is functionally equivalent to RPTPβ-CAH or the RPTPβ-CAH peptide from which it is derived. Non-conserved substitutions consist of replacing one or more amino acids of the RPTPβ-CAH peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues ranging from 2 to 500 amino acids in length. One or more insertions may be introduced into RPTPβ-CAH or into fragments, analogs or homologs thereof (described below).

Deletions of RPTPβ-CAH, RPTPβ-CAH fragments, analogs, and/or RPTPβ-CAH homologs are also within the scope of the invention. Such deletions consist of the removal of one or more amino acids from the RPTPβ-CAH or RPTPβ-CAH-like peptide sequence, with the lower limit length of the resulting peptide sequence being 4 to 6 amino acids. Such deletions may involve a single contiguous or greater than one discrete portion of the peptide sequences.

The peptides of the invention may further include homologs of RPTPβ-CAH and/or RPTPβ-CAH truncations which mimic, enhance, or inhibit the contactin mediated effects of RPTPβ-CAH on neuronal cells. Such RPTPβ-CAH homologs are peptides whose amino acid sequences are comprised of the amino acid sequences of peptide regions of other biological species that correspond to RPTPβ-CAH.

The peptides of the invention may be made by any of the many known methods of synthesis in the chemical or biological arts. By way of example but not by way of limitation, the following methods may be used. Chemical synthesis of polypeptides from amino acid stocks may be used and is described in detail in Creighton, 1984, Proteins, W. H. Freeman and Company, N. Y., especially Chapter 1, which is incorporated by reference herein in its entirety. Biological methods for producing the peptides or polypeptides of the invention include eucaryotic and procaryotic expression systems which have been transfected with nucleic acid encoding the peptides or polypeptides of the invention. These expression systems include, but are not limited to, those employing COS-7 cells as set forth in the examples infra. Preferred expression systems and other biological methods for producing the peptides and polypeptides of the invention are described in detail in Sambrook et al., 1987, Molecular Cloning a Laboratory Manual, Cold Spring Harbor Laboratory, N.Y., Chapters 16–18, which are incorporated by reference herein in their entirety. Preferred expression systems also include Fab expression libraries, as described in Huse et al., 1989, Science, 246:1275–1281, and phage display libraries, as described in Clarkson and Wells, 1994, TIBTEK, 12:173–184, which are both incorporated by reference herein in their entirety.

While not being limited to any theory or explanation of how the invention works, the following is hypothesized to explain which peptides corresponding to the CAH domain of RPTPβ may mimic, enhance or inhibit the contactin mediated effects of RPTPβ-CAH on neuronal cells. The peptides of the invention may exhibit no CAH activity, as is hypothesized to be the case with RPTBβ and y (Barnea et al., 1993, Mol. Cell. Biol., 13:1497–1506). The peptides of the invention may comprise those moieties of RPTPβ-CAH which are necessary to result in a conformational epitope having the ability to mimic, enhance or inhibit the contact mediated effects of RPTPβ-CAH on neuronal cells. These moieties may include the highly packed hydrophobic core and hydrophobic exposed residues which are conserved among the CAH domains of other proteins (Barnea et al., 1993, Mol. Cell. Biol., 13:1497–1506). Because RPTBβ does not bind contactin, the peptides of the invention may comprise those amino acids at the amino-terminal region of RPTPβ which diverge from RPTPβ and the CAH domains of other proteins. The peptides of the invention may also include those moieties of RPTPβ-CAH produced using random expression libraries as described above and then selected by the methods and assays of the invention.

Any of the peptides of the invention may be identified as having the ability to mimic, enhance, or inhibit the contactin mediated effects of RPTPβ-CAH on neuronal cells by any of the methods and assays of the invention as described more fully in section 5.2 above.

5.4. PHARMACEUTICAL FORMULATIONS AND ROUTES OF ADMINISTRATION

Any of the identified compounds can be administered to an animal host, including a human patient, by itself, or in pharmaceutical compositions where it is mixed with suitable carriers or excipient(s) at doses therapeutically effective to treat or ameliorate a variety of disorders, including those characterized by insufficient, aberrant, or excessive neurite growth, differentiation or survival, including but not limited to: ALS; general ataxia; Parkinson's disease; Alzheimer's disease; Huntington's disease; general neropathy; cerebral palsy; neurologic trauma; and mental retardation. A therapeutically effective dose further refers to that amount of the compound sufficient to result in amelioration of symptoms associated with such disorders. Techniques for formulation and administration of the compounds of the instant application may be found in "Remington's Pharmaceutical Sciences," Mack Publishing Co., Easton, Pa., latest edition.

5.4.1. EFFECTIVE DOSAGE

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the desired effects. For examples with respect to the therapeutic peptides and polypeptides that can be used in accordance with the invention, usual patient dosages for systemic administration range from 1–2000 mg/day, commonly from 1–250 mg/day, and typically from 10–150 mg/day. Stated in terms of patient body weight, usual dosages range from 0.02–25 mg/kg/day, commonly from 0.02–3 mg/kg/day, typically from 0.2–1.5 mg/kg/day. Stated in terms of patient body surface areas, usual dosages range from 0.5–1200 $mg/m^2$/day, commonly from 0.5–150 $mg/m^2$/day, typically from 5–100 $mg/m^2$/day. Dosage amount and interval may be adjusted individually to provide plasma levels of the active moiety which are sufficient to maintain the desired effects. Usual average plasma levels should be maintained within 50–5000 μg/ml, commonly 50–1000 μg/ml, and typically 100–500 μg/ml.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.4.2. COMPOSITION AND FORMULATION

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration,the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

5.4.3. ROUTES OF ADMINISTRATION

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

5.4.4. PACKAGING

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of a neurologic disease such as one characterized by insufficient, aberrant, or excessive neurite growth, differentiation or survival.

RPTPβ/ζ is a receptor-type tyrosine phosphatase that is expressed predominantly in the developing nervous system. Its extracellular domain consists of a carbonic anhydrase-like motif (CAH), a fibronectin type III repeat (FNIII) and a long spacer region. In the examples described infra, fusion proteins containing these different subdomains fused to the Fc portion of human IgG were used to screen a panel of neuronal cells to search for ligands for RPTPβ. This screen identified two potential cell associated ligands that are expressed either in neurons or in glial cells. The CAH domain construct (βC-Fc) bound to neuronal cells lines while the addition of the FNIII (βCF-Fc) enabled the interaction of RPTPβ with glial cell lines. Cross-linking experiments identified that the CAH domain bound to a protein of 140 kDa in IMR-32 neuroblastoma and GH3 anterior pituitary cell lines. Expression cloning in COS7 cells revealed that the gene encoding this ligand was the rat homologue of the neural cell recognition molecule contactin (F11/F3). This protein consists of six C2 type Ig domains, four fibronectin type III repeats and a hydrophobic region that mediates its attachment to the membrane by a GPI anchor. Transfection of COS7 cells with rat or human contactin cDNA resulted in binding of RPTPβ, and treatment with phospholipase C completely abolished the binding of βCF-FC to the cells. In addition, soluble contactin-Fc fusion bound to COS cells expressing a chimeric receptor that contained the extracellular region of RPTPβ. Finally, it was found that the CAH domain of RPTPβ induced cell adhesion and neurite growth of primary tectal neurons, and differentiation of IMR-32 neuroblastoma cells. This response could be completely blocked with antibodies against contactin, demonstrating that contactin is the neuronal receptor for RPTPβ. The ability of a receptor-type tyrosine phosphatase to serve as a ligand for a GPI-linked cell recognition molecule illustrates the potential bidirectional nature of information flow during neural growth and development.

6. EXAMPLE: THE INTERACTION BETWEEN CONTACTIN AND THE CAH DOMAIN OF RPTPβ

The subsections below describe the biological interaction between contactin and the CAH domain of RPTPβ. The data demonstrate that ligands for RPTPβ are differentially expressed in neuronal and glial cell lines. In addition, it is shown that a 140 kDa protein from these cell lines interacts with the CAH domain of RPTPβ, and that this 140 kDa protein is contactin. The data also demonstrate that RPTPβinteracts with both membrane-bound and soluble contactin.

6.1. MATERIALS AND METHODS

6.1.1. CELL CULTURE

SF763T and SF767T human astrocytoma cell lines were grown in athymic nu/nu mice to create a tumor derived cell line. The parental lines (SF763 and SF767) were generously provided by Dr. Michael E. Bernes (The Barrow Neurological Institute, Phoenix, Ariz.). All other cell line used were supplied by the American Type Culture Collection (Rockville, Md.). For culturing of rat sensory neuron, spinal sensory ganglia were dissected from newborn rat pups and dissociated by incubation with trypsin (0.05% for 10 minutes). The ganglia were washed several times in L15+ 10% fetal calf serum, and triturated with a pasteur pipette. The resulting single cell suspension was not subjected to preplating. The cells were plated at 15,000 cells per well in an eight-well chamber slide (Nunc) precoated with 10 mg/ml laminin in PBS. The medium was L15/$CO_2$ with supplements as described (Hawrot and Patterson, 1979, Meth. Enzymol., 58:547–584), and nerve growth factor was added at 50 ng/ml. The cells were cultured for two days prior to staining.

6.1.2. GENERATION AND PRODUCTION OF FC-FUSIONS

To construct the Fc-fusion molecule, different subdomains of RPTPβextracellular region were amplified using pfu (Stratagene, La Jolla, Calif.) and cloned into a unique BamHI site upstream from the hinge region of human IgG1-Fc. For the construction of βC and βCF fusions a DNA fragment was amplified from position -20, within the Bluescript sequence to position 939 and 1245 respectively (βC-Fc aa 1-313, βCF-Fc aa 1-415) (Levy et al., 1993, J. Biol. Chem., 268:10573–10581). In frame fusion was made by creating a BamHI site in the 3' primer maintaining the original amino acids sequence in the fusion junction. These fragments were further cloned into HindIII-BamHI linearized pCγ1 vector, a modified version of pIG1 that contained a cDNA form instead of the genomic fragment of human IgG (Simmons, 1993, in Cellular Interactions in Development. A Practical Approach, Hartley (ed.), IRL Press). The same strategy was used to construct human contactin-Fc (Hcon-Fc) fusion molecule. Briefly, total RNA was prepared from Y79 retinoblastoma cells and converted to single strand cDNA using SuperScript II reveres transcriptase (Gibco-BRL) following the suppliers protocol. This cDNA was use as a template to clone human contactin by three overlapping PCR reactions into EcoRI-BamHI sites of pCγ1 vector. In order to use these sites, the EcoRI site at position 3173 (Reid et al., 1994, Brain Res. Mol. Brain Res., 21:1–8), was eliminated by changing a single base during the PCR reaction. The final construct contained amino acids 1–1020 of human contactin fused to the IgG region. To construct βF-Fc the region between nucleotides 901 to 1242 was amplified with a set of primers that introduced SacII and BamHI sites in the ends of the fragment. This fragment was cloned into pCNγ1 between the globulin gene and a sequence encoding a signal peptide derived from TGFβ gene (Plowman et al., 1992, J. Biol. Chem., 267:13073–13078). The integrity of all the above constructs was checked by complete nucleotide sequence determination or by restriction enzyme analysis. Fusion proteins were produced transiently in COS7 cells or by cotransfection with pN1012-Neo into 293 cells and selecting for individual G418 resistant clones as described (Peles et al., 1991, EMBO J., 10:2077–2086). Purification of fusion proteins was achieved by affinity chromatography on Protein-A Sepharose CL 4B (Pharmacia). Bound proteins were eluted with 100 mM sodium citrate PH 2.5, 1M $MgCl_2$, followed by buffer exchange on a PD-10 desalting column (Pharmacia). The proteins were analyzed by gel electrophoresis followed by silver staining (ICN, Costa Mesa, Calif.). Concentration of the purified proteins was determined by bradford reagent (BioRad, Richmond, Calif.), and by an ELISA assay using peroxidase coupled antibody against human IgG (Pierce, Roxford, Ill.). The same antibody was used to detect the fusion proteins by western blotting followed by chemiluminescence reagent (ECL; Amersham) as described previously (Peles et al., 1992, Cell, 69:205–216).

6.1.3. EXPRESSION CLONING IN COS CELLS

Total cellular RNA was prepared from GH3 cells using acid guanidinium thiocyanate extraction (Chomczynski and Sacchi, 1987, Anal. Biochem., 162:156–159), and Poly(A) RNA was isolated by two passages over an oligo dT cellulose column (Pharmacia). cDNA was synthesized using the Superscript kit (Gibco BRL, Bethesda, Md.) by priming with a random primer that contained a HindIII site. Following the addition of EcoRI adaptors the double-stranded cDNA was size selected on agarose gel. cDNAs larger then 2 kb were ligated into a EcoRI and HindIII-digested pcMP1 plasmid vector, a derivative of the pCMV-1 vector (Lammers et al., 1993, J. Biol. Chem., 168:24456–22462). E. coli DH1OB cells (GIBCO BRL) were transformed by electroporation REF. This procedure generated a cDNA library with $2\times10^6$ independent clones. Pools of 3000 bacterial clones were grown for 24 hours and scraped from plates using, LB containing 15% glycerol. Twenty percent of the cultures were saved as glycerol stocks at −70° C. and plasmid DNA was prepared from the rest using the Wizard plasmid purification kit (Promega).

Plasmid DNA (10 μg) was transfected into COS7 cell grown on chamber slides (Nunc) with lipofectamin (GIBCO BRL). After 72 hours cells were incubated for one hour with medium containing 0.5 μg/ml βCF-Fc. Unbound Fc-fusion proteins were removed by three washes with cold DMEM/F12 and the cells were fixed with 4% paraformaldehyd in PBS. Immunostaining was performed with ABC staining system (Vector Lab), using biotinylated anti-human IgG antibodies (Fc specific; Jackson Labs, West Grove, Pa.) following by streptavidin alkaline phosphatase and NBT/BCIP as substrate according to the protocol provided by the manufacturer. One positive pool (#54) was subdivided and rescreened until a single clone (F8) was isolated.

DNA sequence determination was carried out using the dideoxy-chain termination method (Sanger et al., 1977, Proc. Natl. Acad. Sci., USA 74:5463), with Sequenase 2.0 (United States Biochen-Lical Corporation, Cleveland, Ohio). Sequencing was performed on both strands by priming with synthetic oligonucleotides.

6.1.4. CONSTRUCTION OF RPTPβ/EGF-RECEPTOR CHIMERAS

To generate a plasmid for the expression of βCF/EK chimeras, a portion of the extracellular domain of RPTPβcontaining the CAH and the FINIII domains (βCF, aa 1-418) was fused to the human EGF receptor at position 634, twelve amino acids after the transmembrane domain in its extracellular region. These fragments were amplified using pfu (Stratagene, La Jolla, Calif.) with a specific set of primers that introduce a BstBI site at the junction between the two genes. The resulting fragments were ligated into Bluescript (Stratagene, La Jolla, Calif.). Proper fusion between the two molecules was verified by nucleotide sequence analysis. This chimeric gene was then subcloned into a NotI site in the reteroviral vector SRα-SL and viral stocks where prepared by cotransfecting COS-7 cells with this vector along with a helper virus plasmid (Muller et al., 1991, Mol. Cell. Biol., 11:1785–1792). These viruses where used to infect NIH 3T3 (clone 2.2), which lack endogenous EGF-receptor. Following infection, cells where selected in a medium containing 1 mg/ml G418 (Gibco-BRL) and resistant colonies were individually grown and assayed for the expression of the chimeric receptor by Western blotting with antibodies against the carboxyl terminus of the EGF-R (Kris et al., 1985, Cell, 40:619–625) as described previously (Peles et al., 1992, Cell, 69:205–216).

6.1.5. BINDING OF FC-FUSION PROTEINS

Confluent monolayer of cells were incubated for one hour with conditioned medium containing 0.25–0.5 mg/ml Fc-fusion protein. The unbound proteins were removed by three washes with binding medium (0.1% BSA, 0.2% none fat dry milk in DMEM/F12) and the cells were further incubated with 1 ng/ml [$^{125}$I]-Protein A (Amersham), for 30 minutes at 4° C. Plates were washed three times with cold binding medium and cell bound radioactivity was determined as described previously (Peles et al., 1993, EMBO J., 12:961–971). Cellular staining using the Fc-fusion proteins was done using the procedure described above for expression cloning.

15 6.1.6. CHEMICAL CROSS-LINKING EXPERIMENTS

Cells were incubated for four hours with medium containing, the different Fc-fusion proteins. Following three washes with cold PBS/Ca (1 mM $CaCl_2$ in PBS), the cells were incubated for additional 30 minutes with PBS/Ca containing 1 mM DTSSP (3,3'-Dithiobis[sulfosuccinimidyl-propionate], Pierce, Rockford, Ill.). Free cross-linker was removed by additional PBS wash followed by quenching with 100 mM glycine in TBS for 10 minutes at 4° C. Cell lysates were made in SBN lysis buffer (Peles et al., 1991, EMBO J., 10:2077–2086), and Sepharose-protein A was added to the cleared lysates. Following two hours incubation at 4° C., the beads were washed three times with HNTG buffer (Peles et al., 1991, EMBO J., 10:2077–2086), and the bound proteins were eluted by adding SDS PAGE sample buffer containing 5% β-mercaptoethanol and further incubation for 10 minutes at 95° C.

6.1.7. PROTEIN PURIFICATION AND SEQUENCING

Cellular membranes were prepared from $5\times10^8$ GH3 cells by homogenization in hypotonic buffer that included 10 mM Hepes pH 7.5, 1 mM EGTA, 1 mM $MgCl_2$, 10 μg/ml aprotinin, 10 μg/ml leupeptin and 2 mM PMSF. Nuclei and unbroken cells were removed by low speed centrifugation (1000 g×10 minutes at 4° C.), and the supernatant was then subjected to high speed centrifugation at 40000 g (30 minutes at 4° C.). The membrane pellet was resuspended in SML solubilization buffer (2% Sodium monolaurate, 2 mM MgCl2, 2 mM PMSF in PBS). After one hour incubation on ice the detergent-insoluble materials was removed by centrifugation, and the sample was diluted tenfold with PBS containing 2 mM $MgCl_2$. This sample was loaded on a column of βCF-FC bound to Sepharose Protein A (200 μg βCF-Fc/ml beads) at 40° C. The column was washed with SML buffer containing 0.15% detergent and the bound proteins were eluted by adding SDS sample buffer and heating to 95° C. Proteins were separated on 7.5% gel and electroblotted in CAPS buffer (100 mM CAPS, 10% MeOH) to ProBlott membrane (Applied Biosystems). The membrane was stained with coomassie R-250 and the 140 kDa band was excised and subjected to direct microsequencing analysis. Microsequencing was performed with an Applied Biosystems Model 494 sequencer, run using standard reagents and programs from the manufacturer.

To obtain internal peptide sequence the blotted band was moistened with neat acetonitrile, then reduced by the addition of 200 ul of 0.1M Tris pH 8.5, 10 mM dithiothreitol, 10% acetonitrile. After incubation at 55° C. for 30' the sample was cooled to room temperature and 20 ul of 0.25M 4-vinylpyridine in acetonitrile added. After 30 minutes at room temperature the blots were washed 5 times with 10% acetonitrile. Digestion was performed for 16 hours with 1 ug modified trypsin (Promega) in 50 ul of 0.1M Tris pH 8.0, 10% acetonitrile, 1% octylglucoside. Digestion was stopped by the addition of 2 ul of neat trifluoroacetic acid (TFA). Peptides were separated on a 1 mm×200 mm Reliasil C-18 reverse phase column on a Michrom UMA HPLC run at 50 ul per minute. Solvents used were 0.1% TFA in water and 0.085% TFA in 95% acetonitrile/5% water. A linear gradient of 5 to 65% B was run over 60 minutes. Absorbance was monitored at 214 nm and peaks were collected manually into a 96 well polyethylene microtitre plate. Purified peptides were sequenced as described above.

6.1.8. TREATMENT WITH PI-PLC

Cells grown to confluency in 90 mm dishes were metabolically labeled with 100 μg Ci/ml [$^{35}$S]-methionine and cysteine mix (NEN, Boston, Mass.) for four hours at 37° C. Labeled cells were washed three times with MEM and incubated with 250 mU of phosphatidylinositol specific phospholipase C (PI-PLC, Boehringer Mannheim or a kind gift from Dr. J. Salzer) for 50 minutes at 37° C. The supernatant was collected and cleared by centrifugation (1000 g), membranes were prepared from the cells and further solubilized in SML buffer as described above. βCF-Fc bound to Sepharose-protein A beads was added to the supernatant and the membrane fractions for one hour at 4° C. The beads were washed twice with 0.15% sodium monolaurate in PBS and once in PBS before the addition of SDS sample buffer. The precipitated proteins were separated on 7.5% cell and subjected to autoradiography.

For binding experiments, cell were treated with different amounts of PI-PLC (as indicated in the legend to the figures) in MEM containing 0.5% BSA for 30–60 minutes at 37° C. Cells were briefly washed and binding of βCF-Fc was performed as described above.

6.2. RESULTS

6.2.1. THE CAH DOMAIN OF RPTPβ MEDIATES AN INTERACTION WITH NEURONS

To identify cellular ligands for RPTPβ, fusion proteins were constructed between different subdomains of RPTPβ and the Fc portion of human IgG. Three chimeric constructs were made, one containing both the carbonic anhydrase and the fibronectin domains (βCF-Fc) and two others carrying each domain by itself (βC-FC or βF-FC; FIG. 1A and 1B).

Initially, βCF-Fc was used to screen for a membrane bound ligand on the surface of different neuronal and glial cell lines. As shown in FIG. 1C, several cell lines that bind this fusion protein were identified. These were the IMR-32 neuroblastoma cells, the two closely related neuroendocrine derived cell lines GH3 and GH1, and five different glioblastoma cell lines.

The fact that these positive cell lines were derived from glial and neuronal origins raised the possibility that RPTPβ may interact with two different membrane-associated ligands. Alternatively, a single ligand may exist which is expressed by both neurons and glia cells. To explore these two possibilities it was examined whether a fusion protein that contained only the CAH domain of RPTPβ (βC-Fc) will retain the same cell specificity observed with βCF-FC. It was reasoned that in a multidomain receptor like RPTPβ, each domain might function as an independent unit in terms of its interaction with a specific ligand. Thus, the use of a single domain in binding experiments might allow the identification of a cell type specific ligand. As depicted in FIG. 2A, this fusion protein, indeed, binds to the same neuronal and neuroendocrine cell lines. In contrast, none of the glioblastomas were positive, suggesting that there are at least two ligands for RPTPβ that are differentially expressed on neuronal or glial cells. This result also implied that the CAH domain mediates the interaction of RPTPβ with a specific ligand present in neurons but not in glia cells.

Accordingly, if the binding of βC-FC to neuronal ligand reflects the interactions occurring in vivo, one would expect to see similar binding specificity on cultures of primary neurons. The binding of the different fusion proteins to cultured dorsal root ganglion cells (DRG), followed by detection of the bound proteins by immunostaining (FIG. 2B), was analyzed. βC-FC and βCF-FC bound to GH3 cells, as well as to the primary neurons. A fusion protein containing the fibronectin domain alone (βF-Fc) failed to bind to either GH3 cells or DRG neurons (FIG. 2B). In other experiments, binding of βF-FC to several glial cell lines was detected, but no binding of this domain to neuronal derived cell lines or neurons derived from rat DRGs and chick cortex was detected. In addition, it was examined whether the binding specificity observed with the CAH domain of RPTPβ is unique to this receptor by comparing it with the related phosphatase RPTPγ (Barnea et al., 1993, Mol. Cell. Biol., 13:1497–1506). A fusion protein made with the CAH domain of this highly homologous family member did not bind to GH3 cells or to primary neurons (FIG. 2C).

Altogether these results suggests that specific ligands for RPTPβ exist on the surface of cells from neuronal and glial origin. Different subdomains of the receptor mediate its interaction with those distinct ligands. The CAH mediates an interaction with neurons while the FNIII enables the interaction of RPTPβ with glia cells. In the work presented here, the identification and molecular characterization of the ligand for the CAH domain is described.

6.2.2. COVALENT CROSS LINKING EXPERIMENTS REVEAL A 140 KDA PROTEIN THAT INTERACTS WITH THE CAH DOMAIN OF RPTPβ

Figure 3:
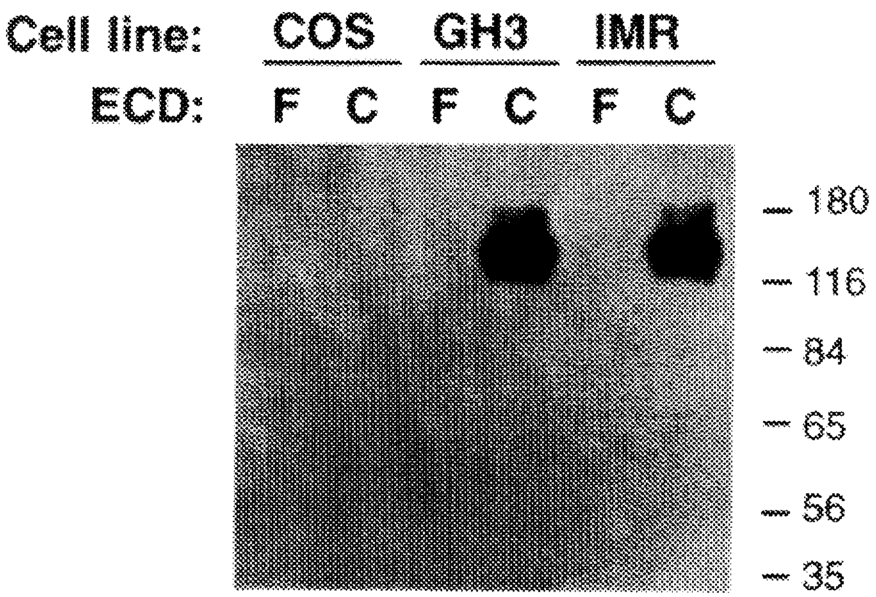

To characterize ligands for RPTPβ, a reversible cross-linker (DSSTP) was used, and proteins were sought that specifically bound to βC-Fc. Two of the cell lines that bound βC-Fc (IMR32 and GH3), as well as COS7 cells as a control, were allowed to react with the fusion proteins containing the FNIII or the CAH domains followed by cross-linking and precipitation of the complexes. As shown in FIG. 3, a protein of about 140 kilodalton specifically reacted with βC-Fc in the rat GH3 and human IMR-32 cells. No reactivity was detected in control cells or in cells incubated with βF-Fc. The cross-linker (DSSTP) used, undergoes cleavage in the reducing SDS PAGE conditions and, therefore, permits the identification of the true molecular weight of the putative ligand. This result suggested that the same ligand is expressed in the rat GH3 and the human IMR-32 lines.

6.2.3. MOLECULAR CLONING OF A CANDIDATE LIGAND FOR RPTPβ FROM RAT GH3 CELLS REVEALS THE RAT HOMOLOGUE OF CONTACTIN

An expression cloning strategy was employed in an effort to clone the gene that encodes the 140 kDa candidate ligand. we have employed. Plasmid pools made from a GH3-cDNA library were transfected into COS7 cells and the cells were screened for their ability to bind βCF-Fc. Positive cells were detected by immunostaining with biotinylated anti-human IgG antibodies and streptavidin alkaline phosphatase. One positive pool was identified that when transfected yielded several stained cells on the slide (FIG. 4A). This pool was subdivided and rescreened four times until a single clone (F8) was isolated. Transfection of COS7 cells with this plasmid resulted in positive staining of approximately 25%–50% of the cells, a number that correlates well with the maximum transfection efficiency in our system. DNA sequence analyses of clone F8 showed that it contained a 3.9 kb insert and a single long open reading frame of 3063 nucleotides. The deduced 1021 amino acid sequence encoded by this clone is presented in FIG. 4B. Data bank search with this sequence showed that it shares 95% and 99% identity at the amino acid level with human and mouse contactin respectively (Berglund and Ranscht, 1994, Genomics, 21:571–582; Gennarini et al., 1989, J. Cell. Biol., 109:755–788; Reid et al., 1994, Brain Res. Mol. Brain Res., 21:1–8). It was therefore concluded that the ligand for RPTPβ cloned from GH3 cells is the rat homologue of contactin. Structurally, this protein consists of six C2 type Ig domains, four fibronectin type III repeats and an hydrophobic region that mediates its attachment to the membrane by a GPI linkage (FIG. 4B., and Gennarini et al., 1989, J. Cell. Biol., 109:755–788; Reid et al., 1994, Brain Res. Mol. Brain Res., 21:1–8). Functionally, it is a neural cell adhesion molecule that has been suggested to play a morphogenic role during the development of the nervous system (Rathjen et al., 1987, J. Cell. Biol., 104:343–353; Walsh and Doherty, 1991, Cell. Biol. Int. Rep., 15:1151–1166).

In parallel to the expression cloning strategy, and as a complementary approach, a biochemical procedure was employed that utilized the CAH domain as an affinity reagent for protein purification. p140 was purified from solubilized membranes prepared from GH3 cells on a column of βCF-Fc (FIG. 4C). After resolving the eluted protein on SDS/PAGE, the 140 kDa species was subject directly to N-terminal sequencing, or was digested with trypsin. Two peptide sequences obtained, one from the N-terminus and the other from an internal peptide after tryptic digest. Both sequences matched the translated F8 sequence and confirmed that contactin is indeed a ligand for the CAH domain of RPTPβ.

6.2.4. BINDING ANALYSIS OF RPTPB AND CONTACTIN

The binding specificity of different subdomains of RPTPβ towards contactin was examined. COS7 cells were transfected with rat contactin (clone F8) and analyzed for their ability to bind fusion proteins containing the CAH, FNIII or both domains (FIG. 5A). As expected, expression of contactin enabled the binding of the CAH domain of RPTPβ to the cells. The FNIII domain alone did not bind to contactin expressing cells. In addition, similar results were obtained with a fusion protein that carries most of the extracellular region of the short form of RPTPβ (aa 1-644; data not shown).

The reciprocal interaction, namely, whether soluble contactin molecules are able to bind specifically to cells expressing RPTPβ, was explored next. In these experiments, COS7 cells were transfected with chimeric receptor constructs that consist of the entire extracellular region of the short form of RPTPβ (βCFS/EK), the CAH domain plus the FNIII repeat (βCF/EK), or the CAH domain alone (βC/EK) fused to the transmembrane and intracellular domains of the EGF receptor. A chimeric receptor was used instead of the wild type phosphatase because the wild type phosphatase was not able to be expressed in heterologous cells. The experiment presented in FIG. 5B, shows that human contactin-Fc fusion protein binds to cells transfected with these chimeric receptors but not to control cells. Taken together, these results demonstrate that expression of contactin is both necessary and sufficient for binding to the CAH domain RPTPβ.

6.2.5. SOLUBLE CONTACTIN RELEASED FROM THE MEMBRANE BY PHOSPHOLIPASE C TREATMENT INTERACTS WITH RPTPβ

Contactin belongs to a family of recognition molecules that TAG-1 and BIG-1, all of which are anchored to the plasma membrane via a glycosyl-phosphatidylinositol (GPI). Therefore, it was of interest to see how phospholipase C (PI-PLC) treatment would effect the interaction between contactin and RPTPβ. When incubated with COS7 cells expressing contactin (clone F8), PI-PLC completely abolished the binding of βCF-Fc to the cells (FIG. 6A). Similar results were obtained also with GH3 cells (FIG. 6B).

It has been demonstrated that members of this family and other GPI-linked proteins may exist either in a membrane bound or a secreted soluble form that is released from the cell surface (Furley et al., 1990, Cell, 61:157–170; Théveniau et al., 1992, J. Cell. Biochem., 48:61–72). Hence, it was examined whether the different forms of contactin, including those released after PI-PLC treatment, could interact with RPTPβ. To this aim, GPI-linked proteins were released from metabolically labeled GH3 cells with the enzyme and purified contactin by bioaffinity precipitation from membrane extracts of the cells or the cell supernatants (FIG. 6C). Without PI-PLC treatment, two proteins p140 and p180 from the membrane fraction could specifically associate with βC-Fc. These proteins were not present in the supernatant and they were not detected with βF-Fc. However, after PI-PLC treatment, p140/contactin could be precipitated from the medium of the cells, indicating that the soluble form produced by phospholipase treatment interacts with RPTPβ. This result may suggest that, in addition to the interaction between the membrane bound forms of these proteins, soluble contactin could potentially interact in vivo with RPTPβ. As shown in FIG. 6C, βC-Fc could precipitate the 180 kilodaltons protein only from membrane fraction and not from the cell supernatant. PI-PLC treatment did not release this protein from the cells suggesting that it is either an integral membrane protein or a cytoskeletal protein associated with contactin complexes. Since contactin by itself is sufficient to mediate the interaction with RPTPβ, the 180 kDa protein may be associated with contactin in the cells and coprecipitated with it during the bioaffinity procedure. One intriguing possibility is that p 180 is a signaling unit used by contactin on the surface of neurons (see below).

7. EXAMPLE: THE CAH DOMAIN OF RPTPβ INDUCES CONTACTIN MEDIATED NEURITE OUTGROWTH

The subsections below describe the induction, by the CAH domain of RPTPβ, of contactin mediated neurite outgrowth. It is shown that the CAH domain of RPTPβ is a permissive substrate for neuronal adhesion and neurite growth. In addition, it is also shown that the neurite growth, differentiation and survival induced by the carbonic anhydrase-like domain of RPTPβ is mediated by neuronal contactin.

7.1. MATERIALS AND METHODS

The materials and methods for this example were the same as those set forth in the example described in section 6.1 above, except as supplemented or amended below.

7.1.1. NEURITE OUTGROWTH ASSAYS

Neurite outgrowth assays using IMR 32 cells were performed as described previously (Friedlander et al., 1994, J. Cell. Biol., 125:669–680) using 35 mm petri dishes coated with different proteins adsorbed on the substrate. After blocking the dishes with 1% BSA/PBS, the blocking solution was replaced with $3\times10^4$ cells suspended in 140 μl of DMEM/F12/ITS. Following incubation for 3 hrs at 37° C. during which time most of the cells adhered to the dish, the medium was removed and replaced with DMEM/FI2/ITS medium containing antibodies (Ig fraction purified by ammonium sulfate precipitation and DE52 chromatography). Dishes were incubated for 48 hrs and fixed with Hanks/0.3% sucrose 2.5% paraformaldehyde. For PI-PLC treatment, primary tectal neurons ($5\times10^4$ cells/250 ml) were prepared from E9 chick embryos (Grumet et al., 1984, Proc. Natl. Acad. Sci. USA, 81:267–271) and incubated with 0.25 μl of PIPLC (1.7 U/ml) in DMEM/F12/ITS+ at 37° C. for 30 min. The cell suspension was then incubated on dishes coated with different substrates without changing the medium.

7.2. RESULTS 7.2.1. NEURITE OUTGROWTH INDUCED BY THE CAH DOMAIN OF RPTPβ IS MEDIATED THROUGH CONTACTIN

Contactin has been shown to be involved in both positive and negative responses of neurons to various stimuli (Br ümmendorf and Rathjen, 1993, J. Neurochem., 61:127–1219). When presented as a ligand to neurons, either as a membrane-bound or a soluble form, contactin induces axonal growth (Brümmendorf et al., 1993, Neuron, 10:711–727; Clarke et al., 1993, Eur. J. Cell. Biol., 61:108–115; Durbec et al., 1992, J. Cell. Biol., 117:877–887; Gennarini et al., 1989, J. Cell. Biol., 109:755–788). Its neural receptor has been identified as the recognition molecule Nr-CAM (Morales et al., 1993, Neuron 11:1113–1122). On the other hand, contactin itself is a receptor present on neurons and mediates their repulsion by the extracellular matrix protein janusin (Pesheva et al., 1993, Neuron, 10:69–82). The results described in the example of Section 6.1 indicate that the CAH domain of RPTPβ can bind to contactin on cells. To analyze effects of this binding on neurons, chick tectal cells, known to express contactin, were plated on dishes previously coated with βCF-Fc fusion protein or with Ng-CAM or laminin as controls. Cells attached and grow processes on both of these substrates (FIG. 7A). Treatment of the cells with PI-PLC prior to plating completely abolished cell attachment and neurite extension on RPTPβ. In contrast, PI-PLC did not have a dramatic effect on cells growing on Ng-CAM or laminin as substrate (FIG. 7A). Thus, it was concluded that the CAH domain of RPTPβis a permissive substrate for neuronal adhesion and neurite growth. Moreover, the cell adhesion and axonal elongation induced by RPTPβ is mediated through a GPI-anchored receptor.

Next it was investigated whether contactin could be the neuronal receptor for the CAH domain of RPTPβ. To this aim, a human neuroblastoma cell line IMR-32 was used that has the capacity to differentiate and to elaborate neurites in response to different stimuli (Lüdecke and Unnsicker, 1990, Cancer, 65:2270–2278). These cells have fibroblastic morphology when crown on petri dishes coated with fibronectin, but on laminin substrates they assume a neuronal phenotype and extend processes with growth cones (FIG. 7B). A similar morphologic differentiation was seen after plating the cells on the CAH domain of RPTPβ. In contrast, the CAH domain of RPTPγ had no effect on cell adhesion and differentiation. These results show that IMR-32 cells respond specifically to the carbonic anhydrase domain of RPTPβ. To determine whether contactin could be acting as a receptor on the IMR-32 cells for RPTPβ, the effects of antibodies against contactin on the growth of cells on different substrates were tested. Antibodies against contactin inhibited the growth of processes on βC-Fc and βCF-Fc but not on laminin (FIG. 7B). In the presence of these antibodies, the IMR-32 cells also retracted their processes and many cells lifted off the dish yielding fewer cells after 2 days of incubation. No effect was observed with control antibodies. Thus, the neurite growth, differentiation and survival induced by the carbonic anhydrase-like domain of RPTPβ is mediated by contactin present in the neurons.

The present invention is not to be limited in scope by the exemplified embodiments which are intended as illustration of single aspects of the invention, and any clones, DNA or amino acid sequences which are functional equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 270 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:1:

-continued

| | | | | | | | | | | | | | | | |
|---|---|---|---|---|---|---|---|---|---|---|---|---|---|---|---|
| Lys | Leu | Val | Glu | Glu | Ile | Gly | Trp | Ser | Tyr | Thr | Gly | Ala | Leu | Asn | Gln |
| 1 | | | | 5 | | | | | 10 | | | | | 15 | |
| Lys | Asn | Trp | Gly | Lys | Lys | Tyr | Pro | Thr | Cys | Asn | Ser | Pro | Lys | Gln | Ser |
| | | | 20 | | | | | 25 | | | | | 30 | | |
| Pro | Ile | Asn | Ile | Asp | Glu | Asp | Leu | Thr | Gln | Val | Asn | Val | Asn | Leu | Lys |
| | | 35 | | | | | 40 | | | | | 45 | | | |
| Lys | Leu | Lys | Phe | Gln | Gly | Trp | Asp | Lys | Thr | Ser | Leu | Glu | Asn | Thr | Phe |
| | 50 | | | | | 55 | | | | | 60 | | | | |
| Ile | His | Asn | Thr | Gly | Lys | Thr | Val | Glu | Ile | Asn | Leu | Thr | Asn | Asp | Tyr |
| 65 | | | | | 70 | | | | | 75 | | | | | 80 |
| Arg | Val | Ser | Gly | Gly | Val | Ser | Glu | Met | Val | Phe | Lys | Ala | Ser | Lys | Ile |
| | | | | 85 | | | | | 90 | | | | | 95 | |
| Thr | Phe | His | Trp | Gly | Lys | Cys | Asn | Met | Ser | Ser | Asp | Gly | Ser | Glu | His |
| | | | 100 | | | | | 105 | | | | | 110 | | |
| Ser | Leu | Glu | Gly | Gln | Lys | Phe | Pro | Leu | Glu | Met | Gln | Ile | Tyr | Cys | Phe |
| | | 115 | | | | | 120 | | | | | 125 | | | |
| Asp | Ala | Asp | Arg | Phe | Ser | Ser | Phe | Glu | Glu | Ala | Val | Lys | Gly | Lys | Gly |
| | 130 | | | | | 135 | | | | | 140 | | | | |
| Lys | Leu | Arg | Ala | Leu | Ser | Ile | Leu | Phe | Glu | Val | Gly | Thr | Glu | Glu | Asn |
| 145 | | | | | 150 | | | | | 155 | | | | | 160 |
| Leu | Asp | Phe | Lys | Ala | Ile | Ile | Asp | Gly | Val | Glu | Ser | Val | Ser | Arg | Phe |
| | | | | 165 | | | | | 170 | | | | | 175 | |
| Gly | Lys | Gln | Ala | Ala | Leu | Asp | Pro | Phe | Ile | Leu | Leu | Asn | Leu | Leu | Pro |
| | | | 180 | | | | | 185 | | | | | 190 | | |
| Asn | Ser | Thr | Asp | Lys | Tyr | Tyr | Ile | Tyr | Asn | Gly | Ser | Leu | Thr | Ser | Pro |
| | | 195 | | | | | 200 | | | | | 205 | | | |
| Pro | Cys | Thr | Asp | Thr | Val | Asp | Trp | Ile | Val | Phe | Lys | Asp | Thr | Val | Ser |
| | 210 | | | | | 215 | | | | | 220 | | | | |
| Ile | Ser | Glu | Ser | Gln | Leu | Ala | Val | Phe | Cys | Glu | Val | Leu | Thr | Met | Gln |
| 225 | | | | | 230 | | | | | 235 | | | | | 240 |
| Gln | Ser | Gly | Tyr | Val | Met | Leu | Met | Asp | Tyr | Leu | Gln | Asn | Asn | Phe | Arg |
| | | | | 245 | | | | | 250 | | | | | 255 | |
| Glu | Gln | Gln | Tyr | Phe | Ser | Arg | Gln | Val | Phe | Ser | Ser | Tyr | Thr | | |
| | | | 260 | | | | | 265 | | | | | 270 | | |

( 2 ) INFORMATION FOR SEQ ID NO:2:

( i ) SEQUENCE CHARACTERISTICS:
( A ) LENGTH: 1018 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Lys | Thr | Pro | Leu | Leu | Val | Ser | His | Leu | Leu | Leu | Ile | Ser | Leu | Thr |
| 1 | | | | 5 | | | | | 10 | | | | | 15 | |
| Ser | Cys | Leu | Gly | Glu | Phe | Thr | Trp | His | Arg | Arg | Tyr | Gly | His | Gly | Val |
| | | | 20 | | | | | 25 | | | | | 30 | | |
| Ser | Glu | Glu | Asp | Lys | Gly | Phe | Gly | Pro | Ile | Phe | Glu | Glu | Gln | Pro | Ile |
| | | 35 | | | | | 40 | | | | | 45 | | | |
| Asn | Thr | Ile | Tyr | Pro | Glu | Glu | Ser | Leu | Glu | Gly | Lys | Val | Ser | Leu | Asn |
| | 50 | | | | | 55 | | | | | 60 | | | | |
| Cys | Arg | Ala | Arg | Ala | Ser | Pro | Phe | Pro | Val | Tyr | Lys | Trp | Arg | Met | Asn |
| 65 | | | | | 70 | | | | | 75 | | | | | 80 |

-continued

Asn Gly Asp Val Asp Leu Thr Asn Asp Arg Tyr Ser Met Val Gly Gly
85 90 95

Asn Leu Val Ile Asn Asn Pro Asp Lys Gln Lys Asp Ala Gly Ile Tyr
100 105 110

Tyr Cys Leu Ala Ser Asn Asn Tyr Gly Met Val Arg Ser Thr Glu Ala
115 120 125

Thr Leu Ser Phe Gly Tyr Leu Asp Pro Phe Pro Pro Glu Asp Arg Pro
130 135 140

Glu Val Lys Val Lys Glu Gly Lys Gly Met Val Leu Leu Cys Asp Pro
145 150 155 160

Pro Tyr His Phe Pro Asp Asp Leu Ser Tyr Arg Trp Leu Asn Glu Phe
165 170 175

Pro Val Phe Ile Thr Met Asp Lys Arg Arg Phe Val Ser Gln Thr Asn
180 185 190

Gly Asn Leu Tyr Ile Ala Asn Val Glu Ser Ser Asp Arg Gly Asn Tyr
195 200 205

Ser Cys Phe Val Ser Ser Pro Ser Ile Thr Lys Ser Val Phe Ser Lys
210 215 220

Phe Ile Pro Leu Ile Pro Ile Pro Glu Arg Thr Thr Lys Pro Tyr Pro
225 230 235 240

Ala Asp Ile Val Val Gln Phe Lys Asp Ile Tyr Thr Met Met Gly Gln
245 250 255

Asn Val Thr Leu Glu Cys Phe Ala Leu Gly Asn Pro Val Pro Asp Ile
260 265 270

Arg Trp Arg Lys Val Leu Glu Pro Met Pro Thr Thr Ala Glu Ile Ser
275 280 285

Thr Ser Gly Ala Val Leu Lys Ile Phe Asn Ile Gln Leu Glu Asp Glu
290 295 300

Gly Leu Tyr Glu Cys Glu Ala Glu Asn Ile Arg Gly Lys Asp Lys His
305 310 315 320

Gln Ala Arg Ile Tyr Val Gln Ala Phe Pro Glu Trp Val Glu His Ile
325 330 335

Asn Asp Thr Glu Val Asp Ile Gly Ser Asp Leu Tyr Trp Pro Cys Val
340 345 350

Ala Thr Gly Lys Pro Ile Pro Thr Ile Arg Trp Leu Lys Asn Gly Tyr
355 360 365

Ala Tyr His Lys Gly Glu Leu Arg Leu Tyr Asp Val Thr Phe Glu Asn
370 375 380

Ala Gly Met Tyr Gln Cys Ile Ala Glu Asn Ala Tyr Gly Thr Ile Tyr
385 390 395 400

Ala Asn Ala Glu Leu Lys Ile Leu Ala Leu Ala Pro Thr Phe Glu Met
405 410 415

Asn Pro Met Lys Lys Lys Ile Leu Ala Ala Lys Gly Gly Arg Val Ile
420 425 430

Ile Glu Cys Lys Pro Lys Ala Ala Pro Lys Pro Lys Phe Ser Trp Ser
435 440 445

Lys Gly Thr Glu Trp Leu Val Asn Ser Ser Arg Ile Leu Ile Trp Glu
450 455 460

Asp Gly Ser Leu Glu Ile Asn Asn Ile Thr Arg Asn Asp Gly Gly Ile
465 470 475 480

Tyr Thr Cys Phe Ala Glu Asn Asn Arg Gly Lys Ala Asn Ser Thr Gly
485 490 495

Thr Leu Val Ile Thr Asn Pro Thr Arg Ile Ile Leu Ala Pro Ile Asn
500 505 510

-continued

| | | | | | | | | | | | | | | | |
|---|---|---|---|---|---|---|---|---|---|---|---|---|---|---|---|
| Ala | Asp | Ile | Thr | Val | Gly | Glu | Asn | Ala | Thr | Met | Gln | Cys | Ala | Ala | Ser |
| | | 515 | | | | | 520 | | | | | 525 | | | |
| Phe | Asp | Pro | Ser | Leu | Asp | Leu | Thr | Phe | Val | Trp | Ser | Phe | Asn | Gly | Tyr |
| | 530 | | | | | 535 | | | | | 540 | | | | |
| Val | Ile | Asp | Phe | Asn | Lys | Glu | Ile | Thr | His | Ile | His | Tyr | Gln | Arg | Asn |
| 545 | | | | | 550 | | | | | 555 | | | | | 560 |
| Phe | Met | Leu | Asp | Ala | Asn | Gly | Glu | Leu | Leu | Ile | Arg | Asn | Ala | Gln | Leu |
| | | | | 565 | | | | | 570 | | | | | 575 | |
| Lys | His | Ala | Gly | Arg | Tyr | Thr | Cys | Thr | Ala | Gln | Thr | Ile | Val | Asp | Asn |
| | | | 580 | | | | | 585 | | | | | 590 | | |
| Ser | Ser | Ala | Ser | Ala | Asp | Leu | Val | Val | Arg | Gly | Pro | Pro | Gly | Pro | Pro |
| | | 595 | | | | | 600 | | | | | 605 | | | |
| Gly | Gly | Leu | Arg | Ile | Glu | Asp | Ile | Arg | Ala | Thr | Ser | Val | Ala | Leu | Thr |
| | 610 | | | | | 615 | | | | | 620 | | | | |
| Trp | Ser | Arg | Gly | Ser | Asp | Asn | His | Ser | Pro | Ile | Ser | Lys | Tyr | Thr | Ile |
| 625 | | | | | 630 | | | | | 635 | | | | | 640 |
| Gln | Thr | Lys | Thr | Ile | Leu | Ser | Asp | Asp | Trp | Lys | Asp | Ala | Lys | Thr | Asp |
| | | | | 645 | | | | | 650 | | | | | 655 | |
| Pro | Pro | Ile | Ile | Glu | Gly | Asn | Met | Glu | Ser | Ala | Lys | Ala | Val | Asp | Leu |
| | | | 660 | | | | | 665 | | | | | 670 | | |
| Ile | Pro | Trp | Met | Glu | Tyr | Glu | Phe | Arg | Val | Val | Ala | Thr | Asn | Thr | Leu |
| | | 675 | | | | | 680 | | | | | 685 | | | |
| Gly | Thr | Gly | Glu | Pro | Ser | Ile | Pro | Ser | Asn | Arg | Ile | Lys | Thr | Asp | Gly |
| | 690 | | | | | 695 | | | | | 700 | | | | |
| Ala | Ala | Pro | Asn | Val | Ala | Pro | Ser | Asp | Val | Gly | Gly | Gly | Gly | Gly | Thr |
| 705 | | | | | 710 | | | | | 715 | | | | | 720 |
| Asn | Arg | Glu | Leu | Thr | Ile | Thr | Trp | Ala | Pro | Leu | Ser | Arg | Glu | Tyr | His |
| | | | | 725 | | | | | 730 | | | | | 735 | |
| Tyr | Gly | Asn | Asn | Phe | Gly | Tyr | Ile | Val | Ala | Phe | Lys | Pro | Phe | Asp | Gly |
| | | | 740 | | | | | 745 | | | | | 750 | | |
| Glu | Glu | Trp | Lys | Lys | Val | Thr | Val | Thr | Asn | Pro | Asp | Thr | Gly | Arg | Tyr |
| | | 755 | | | | | 760 | | | | | 765 | | | |
| Val | His | Lys | Glu | Thr | Met | Thr | Pro | Ser | Thr | Ala | Phe | Gln | Val | Lys | Val |
| | 770 | | | | | 775 | | | | | 780 | | | | |
| Lys | Ala | Phe | Asn | Asn | Lys | Gly | Asp | Gly | Pro | Tyr | Ser | Leu | Ile | Ala | Val |
| 785 | | | | | 790 | | | | | 795 | | | | | 800 |
| Ile | Asn | Ser | Ala | Gln | Asp | Ala | Pro | Ser | Glu | Ala | Pro | Thr | Glu | Val | Gly |
| | | | | 805 | | | | | 810 | | | | | 815 | |
| Val | Lys | Val | Leu | Ser | Ser | Ser | Glu | Ile | Ser | Val | His | Trp | Lys | His | Val |
| | | | 820 | | | | | 825 | | | | | 830 | | |
| Leu | Glu | Lys | Ile | Val | Glu | Ser | Tyr | Gln | Ile | Arg | Tyr | Ala | Gly | His | Asp |
| | | 835 | | | | | 840 | | | | | 845 | | | |
| Lys | Glu | Ala | Ala | Ala | His | Arg | Val | Gln | Val | Thr | Ser | Gln | Glu | Tyr | Ser |
| | 850 | | | | | 855 | | | | | 860 | | | | |
| Ala | Arg | Leu | Glu | Asn | Leu | Leu | Pro | Asp | Thr | Gln | Tyr | Phe | Ile | Glu | Val |
| 865 | | | | | 870 | | | | | 875 | | | | | 880 |
| Gly | Ala | Cys | Asn | Ser | Ala | Gly | Cys | Gly | Pro | Ser | Ser | Asp | Val | Ile | Glu |
| | | | | 885 | | | | | 890 | | | | | 895 | |
| Thr | Phe | Thr | Arg | Lys | Ala | Pro | Pro | Ser | Gln | Pro | Pro | Arg | Ile | Ile | Ser |
| | | | 900 | | | | | 905 | | | | | 910 | | |
| Ser | Val | Arg | Ser | Gly | Ser | Arg | Tyr | Ile | Ile | Thr | Trp | Asp | His | Val | Val |
| | | 915 | | | | | 920 | | | | | 925 | | | |
| Ala | Leu | Ser | Asn | Glu | Ser | Thr | Val | Thr | Gly | Tyr | Lys | Ile | Leu | Tyr | Arg |

-continued

| | | | | | | | | | | | | | | | |
|---|---|---|---|---|---|---|---|---|---|---|---|---|---|---|---|
| | 930 | | | | | 935 | | | | | 940 | | | | |
| Pro<br>945 | Asp | Gly | Gln | His | Asp<br>950 | Gly | Lys | Leu | Phe | Ser<br>955 | Thr | His | Lys | His | Ser<br>960 |
| Ile | Glu | Val | Pro | Ile<br>965 | Pro | Arg | Asp | Gly | Glu<br>970 | Tyr | Val | Val | Glu | Val<br>975 | Arg |
| Ala | His | Ser | Asp<br>980 | Gly | Gly | Asp | Gly | Val<br>985 | Val | Ser | Gln | Val | Lys<br>990 | Ile | Ser |
| Gly | Val | Ser<br>995 | Thr | Leu | Ser | Ser | Gly<br>1000 | Leu | Leu | Ser | Leu | Leu<br>1005 | Leu | Pro | Ser |
| Leu | Gly<br>1010 | Phe | Leu | Val | Phe | Tyr<br>1015 | Ser | Glu | Phe | | | | | | |

What is claimed is:

1. A method for screening a test compound for the ability to alter the effects of the carbonic anhydrase domain of receptor-type phosphataseβ on neuronal cells, which comprises:

(a) growing neuronal cells expressing contactin in the presence of the carbonic anhydrase domain of receptor-type phosphataseβ and in the presence or absence of a test compound in solution, wherein in the absence of said test compound, said contactin and carbonic anhydrase domain bind;

(b) detecting a contactin-mediated characteristic of the neuronal cells, said characteristic selected from the group consisting of cell adhesion, outgrowth, differentiation, survival, and neurite extension; and (c) comparing the characteristics detected in step (b) when the cells are exposed to the test compound with when the cells are not exposed to the test compound, wherein if the test compound enhances, mimics, or inhibits a contactin-mediated characteristic, then the test compound alters the effects of the carbonic anhydrase domain of receptor-type phosphataseβ.

2. The method of claim 1 where the carbonic anhydrase domain of receptor-type phosphataseβ is coated on a solid substrate.

3. The method of claim 1 or claim 2 wherein the test compound is a peptide or protein, and the method further comprises:

(a) binding and covalently linking the test compound to the contactin to form a conjugate;

(b) affinity purifying the conjugate;

(c) cleaving the conjugate to reform the test compound and contactin; and (d) determining the amino acid sequence of the test compound.

4. The method of claim 1 or claim 2 wherein the step of growing the neuronal cells is conducted in the presence of antibodies to contactin.

5. The method of claim 1 or claim 2 wherein the step of growing the neuronal cells is conducted in the presence of phospholipase C.

* * * * *